(12) United States Patent
Kang

(10) Patent No.: US 6,623,989 B2
(45) Date of Patent: Sep. 23, 2003

(54) NONVOLATILE FERROELECTRIC MEMORY AND METHOD FOR FABRICATING THE SAME

(75) Inventor: Hee Bok Kang, Daejeon-si (KR)

(73) Assignee: Hyundai Electronics Industries Co., Ltd., Ichon-shi (KR)

( * ) Notice: Subject to any disclaimer, the term of this patent is extended or adjusted under 35 U.S.C. 154(b) by 0 days.

(21) Appl. No.: 10/205,369

(22) Filed: Jul. 26, 2002

(65) Prior Publication Data
US 2002/0182756 A1 Dec. 5, 2002

Related U.S. Application Data

(62) Division of application No. 09/367,919, filed on Aug. 23, 1999, now Pat. No. 6,462,193.

(30) Foreign Application Priority Data
Aug. 16, 1999 (KR) ............................................ 99-33707

(51) Int. Cl.[7] .............................................. H01L 21/00
(52) U.S. Cl. ...................................................... 438/3
(58) Field of Search ............................................. 438/3

(56) References Cited

U.S. PATENT DOCUMENTS

| | | | |
|---|---|---|---|
| 4,873,664 A | 10/1989 | Eaton, Jr. ................... | 365/145 |
| 5,361,225 A | 11/1994 | Ozawa ....................... | 365/145 |
| 5,680,344 A | 10/1997 | Seyyedy ..................... | 365/145 |
| 5,978,253 A | 11/1999 | Lee et al. .................... | 365/145 |
| 6,046,926 A * | 4/2000 | Tanaka et al. ............... | 365/145 |
| 6,067,244 A | 5/2000 | Ma et al. ..................... | 365/145 |
| 6,278,630 B1 * | 8/2001 | Yamada ...................... | 365/145 |
| 6,301,145 B1 | 10/2001 | Nishihara ................... | 365/145 |
| 6,314,016 B1 | 11/2001 | Takasu ....................... | 365/145 |

* cited by examiner

Primary Examiner—David Nelms
Assistant Examiner—Thao Le
(74) Attorney, Agent, or Firm—Fleshner & Kim, LLP

(57) ABSTRACT

Nonvolatile ferroelectric memory and method for fabricating the same can reduce fatigue caused by repetitive switching, drop an operation voltage, and increase an operation speed of the nonvolatile ferroelectric memory. The nonvolatile ferroelectric memory includes a plurality of wordlines formed in one direction, and a plurality of a control line and a sensing line pairs formed in a direction crossing the wordlines at fixed intervals. Unit cells of the memory formed at intersections of the wordlines and the control and signal line pairs each have first transistors formed between the control line and the sensing line with a drain coupled to a prescribed voltage. Second transistors in the unit cells have a drain coupled to the sensing line, a source coupled to a source of the first transistor, and a gate coupled to the wordline, and third transistors in the unit cells have a drain coupled to the control line, a source coupled to a gate of the first transistor, and a gate coupled to the wordline. The first transistors can have a gate dielectric film formed of a ferroelectric material.

22 Claims, 19 Drawing Sheets

NONVOLATILE FERROELECTRIC MEMORY AND METHOD FOR FABRICATING THE SAME

This application is a division of application Ser. No. 09/367,919, filed Aug. 23, 1999, now U.S. Pat. No. 6,462, 193.

BACKGROUND OF THE INVENTION

1. Field of the Invention

The present invention relates to a semiconductor device, and more particularly, to a nonvolatile ferroelectric memory and a method for fabricating the same.

2. Background of the Related Art

Generally, a nonvolatile ferroelectric memory, i.e., a ferroelectric random access memory (FRAM) has a data processing speed equal to a dynamic random access memory (DRAM) and retains data even in power off. For this reason, the nonvolatile ferroelectric memory has received much attention as a next generation memory device.

The FRAM and DRAM ate memory devices with similar structures, but the FRAM includes a ferroelectric capacitor having a high residual polarization characteristic. The residual polarization characteristic permits data to be maintained even if an electric field is removed.

FIG. 1 shows hysteresis loop of a general ferroelectric. As shown in FIG. 1, even if polarization induced by the electric field has the electric field removed, data is maintained at a certain amount (i.e., d and a states) without being erased due to the presence of residual polarization (or spontaneous polarization). A nonvolatile ferroelectric memory cell is used as a memory device by corresponding the d and a states to 1 and 0, respectively.

A related art nonvolatile ferroelectric memory device will now be described. FIG. 2 shows unit cell of a related art nonvolatile ferroelectric memory.

As shown in FIG. 2, the related art nonvolatile ferroelectric memory includes a bitline B/L formed in one direction, a wordline W/L formed to cross the bitline, a plate line P/L spaced apart from the wordline in the same direction as the wordline, a transistor T1 with a gate connected with the wordline and a source connected with the bitline, and a ferroelectric capacitor FC1. A first terminal of the ferroelectric capacitor FC1 is connected with a drain of the transistor T1 and second terminal is connected with the plate line P/L.

The data input/output operation of the related art nonvolatile ferroelectric memory device will now be described. FIG. 3a is a timing chart illustrating the operation of the write mode of the related art nonvolatile ferroelectric memory device, and FIG. 3b is a timing chart illustrating the operation of read mode thereof.

During the write mode, an externally applied chip enable signal CSBpad is activated from high state to low state. At the same time, if a write enable signal WEBpad is applied from high state to low state, the write mode starts. Subsequently, if address decoding in the write mode starts, a pulse applied to a corresponding wordline is transited from low state to high state to select a cell.

A high signal in a certain period and a low signal in a certain period are sequentially applied to a corresponding plate line in a period where the wordline is maintained at high state. To write a logic value "1" or "0" in the selected cell, a high signal or low signal synchronized with the write enable signal WEBpad is applied to a corresponding bitline.

In other words, a high signal is applied to the bitline, and if the low signal is applied to the plate line in a period where the signal applied to the wordline is high, a logic value "1" is written in the ferroelectric capacitor. A low signal is applied to the bitline, and if the signal applied to the plate line is high, a logic value "0" is written in the ferroelectric capacitor.

The reading operation of data stored in a cell by the above operation of the write mode will now be described. If an externally applied chip enable signal CSBpad is activated from high state to low state, all of bitlines become equipotential to low voltage by an equalizer signal EQ before a corresponding wordline is selected.

Then, the respective bitline becomes inactive and an address is decoded. The low signal is transited to the high signal in the corresponding wordline according to the decoded address so that a corresponding cell is selected.

The high signal is applied to the plate line of the selected cell to destroy data corresponding to the logic value "1" stored in the ferroelectric memory. If the logic value "0" is stored in the ferroelectric memory, the corresponding data is not destroyed.

The destroyed data and the data that is not destroyed are output as different values by the ferroelectric hysteresis loop, so that a sensing amplifier senses the logic value "1" or "0". In other words, if the data is destroyed, the "d" state is transited to an "f" state as shown in hysteresis loop of FIG. 1. If the data is not destroyed, "a" state is transited to the "f" state. Thus, if the sensing amplifier is enabled after a set time has elapsed, the logic value "1" is output in case that the data is destroyed while the logic value "0" is output in case that the data is not destroyed.

As described above, after the sensing amplifier outputs data, to recover the data to the original data, the plate line becomes inactive from high state to low state at the state that the high signal is applied to the corresponding wordline.

FIG. 4 is a block diagram showing the related art nonvolatile ferroelectric memory device. As shown in FIG. 4, the related art nonvolatile ferroelectric memory device includes a main cell array 41, a reference cell array 42 assigned on a lower part of the main cell array 41, a wordline driver 43 formed at a side of the main cell array for applying a driving signal to the main cell array 41 and the reference cell array 42, and a sense amplifier unit 44 formed at a lower part of the reference cell array 42. The wordline driver 43 applies the driving signal to a main wordline of the main cell array 41 and a reference wordline of the reference cell array 42. The sense amplifier unit 44 includes a plurality of sensing amplifiers and amplifies signals of a corresponding bitline B/L and bit bar line BB/L.

The operation of the related art nonvolatile ferroelectric memory device will now be described with reference to FIG. 5. FIG. 5 is a partially detailed view of FIG. 4. As shown in the drawing, the main cell array has a folded bitline structure in the same manner as DRAM.

Also, the reference cell array 42 has a folded bitline structure and includes a reference cell wordline and a reference cell plate line in pairs. At this time, reference cell wordline and the reference cell plate line pairs are defined as RWL__N−1 and RPL__N−1, and RWL__N and RPL__N, respectively.

When the main cell wordline WL__N−1 and the main cell plate line PL__N−1 are activated, the reference cell wordline RWL__N−1 and the reference cell plate line RPL__N−1 are activated. Therefore, data in the main cell is loaded into the bitline B/L and data in the reference cell is loaded into the bit bar line BB/L.

When the main cell wordline WL__N and the main cell plate line PL__N are activated, the reference cell wordline RWL_N and the reference cell plate line RPL_N are activated. Therefore, data in the main cell is loaded into the bit bar line BB/L and data in the reference cell is loaded into the bitline B/L.

A reference voltage REF by the reference cell exists between the bitline levels B_H(high) and B_L(low) by the main cell. To generate the reference voltage REF between the bitline levels B_H and B_L, the logic value "1" or "0" may be stored in a capacitor of the reference cell. When the logic value "1" is stored in the capacitor of the reference cell, the size of the capacitor of the reference cell is smaller than that of the capacitor of the main cell. When the logic value "0" is stored in the capacitor of the reference cell, the size of the capacitor of the reference cell is greater than that of the capacitor of the main cell. Thus, the related art nonvolatile ferroelectric memory can produce a reference voltage required by the sense amplifier unit 44 by using these two methods.

As described above, the related art nonvolatile ferroelectric memory has various disadvantages. When a capacitor size of the reference cell is made smaller than a capacitor size of the main cell to provide a level of the reference voltage to be between the bitline levels B_H and B_L and the reference cell capacitor is excessively switched, in comparison to the main cell, the reference cell experiences fatigue before the main cell, which makes the reference voltage unstable. When a capacitor size of the reference cell is made larger than a capacitor size of the main cell to provide the reference voltage to be between the bitline levels B_H and B_L, the capacitor size is larger.

The above references are incorporated by reference herein where appropriate for appropriate teachings of additional or alternative details, features and/or technical background.

SUMMARY OF THE INVENTION

An object of the invention is to solve at least the above problems and/or disadvantages and to provide at least the advantages described hereinafter.

Another object of the present invention is to provide a nonvolatile ferroelectric memory and a method for fabricating the same that substantially obviates one or more of the problems due to limitations and disadvantages of the related art.

Another object of the present invention is to provide a nonvolatile ferroelectric memory and a method for fabricating the same that has a ferroelectric material for a gate insulating film in a gate electrode of a memory cell.

Another object of the present invention is to provide a nonvolatile ferroelectric memory and a method for fabricating the same that has three electrodes coupled together between first and second crossing signal lines in a memory cell.

Another object of the present invention is to provide a nonvolatile ferroelectric memory and a method for fabricating the same that reduces fatigue caused by the repetitive switching.

Another object of the present invention is to provide a nonvolatile ferroelectric memory and a method for fabricating the same that drops an operational voltage.

Another object of the present invention is to provide a nonvolatile ferroelectric memory and a method for fabricating the same that increases an operational speed.

Another object of the present invention is to provide a nonvolatile ferroelectric memory and a method for fabricating the same that reduces fatigue of a reference capacitor, drops an operations voltages and increases an operational speed.

To achieve at least these objects and other advantages in a whole or in part and in accordance with the purpose of the present invention, as embodied and broadly described, the nonvolatile ferroelectric memory includes a plurality of wordlines formed in one direction, a plurality of pairs each having a control line and a sensing line formed in a direction crossing the wordlines at fixed intervals, first transistors each formed between every pair of the control line and the sensing line having a drain applied of a power source voltage and a gate dielectric film formed of a ferroelectric material, second transistors each having a drain connected to the sensing line, a source connected to a source of the first transistor, and a gate connected to the wordline, and third transistors each having a drain connected to the control line, a source connected to a gate of the first transistor, and a gate connected to the wordline.

To further achieve the above objects in a whole or in part and in accordance with the purpose of the present invention, as embodied and broadly described, a method for fabricating a nonvolatile ferroelectric memory includes (1) forming a first insulating layer at a depth in a semiconductor substrate in a horizontal direction, and forming a second insulating layer arranged from a surface of the substrate to ends of the first insulating layer, to define the semiconductor substrate as a first substrate and a second substrate, (2) forming a first gate electrode over the first substrate with a ferroelectric material disposed inbetween, (3) forming a second gate electrode and a third gate electrode over the second substrate on both sides of the first substrate, each with a gate insulating film disposed inbetween, (4) forming first source/drain regions of a conduction type opposite to the first substrate in the first substrate on both sides of the first gate electrode, (5) forming second, and third source/drain regions of a conduction type opposite to the second substrate in the second substrate on both sides of the second and third gate electrodes, and (6) forming a first impurity region of a conduction type identical to the first substrate in the first substrate on one side of the first source impurity region.

To further achieve the above objects in a whole or in part and in accordance with the purpose of the present invention, as embodied and broadly described, a memory device, comprising a plurality of first signal lines extending along a first direction, a plurality of second signal lines extending along a second direction to cross the first signal lines at prescribed intervals, a memory array having memory cells corresponding to intersections of the first signal lines and the second signal lines, a driver coupled to the first signal lines, a decoder coupled to the second signal lines, a sensing circuit coupled to the second signal lines to output data from the memory array, wherein each memory cell includes a transistor having a gate insulating layer of a gate electrode being a material that exhibits a residual polarization after application of an electric field.

To further achieve the above objects in a whole or in part and in accordance with the purpose of the present invention, as embodied and broadly described, a memory device, comprising a plurality of first signal lines extending along a first direction, a plurality of second signal line pairs extending along a second direction to cross the first signal lines at prescribed intervals, a memory array having unit cells corresponding to intersections of the first signal lines and the second signal line pairs, a driver coupled to the first signal lines, a decoder coupled to the second signal lines, a sensing circuit coupled to the second signal lines to output data from the memory array, wherein a unit cell comprises, a first transistor coupled between a first pair of the second signal line pairs having a second electrode coupled to a first reference voltage, a second transistor having a second electrode coupled to one of the first pair of the second signal line pairs, a first electrode coupled to a first electrode of the first transistor, and a control electrode coupled to a corresponding first signal line; and a third transistor having a second electrode coupled to the other one of the first pair of the second signal line pairs, a first electrode coupled to a control electrode of the first transistor, and a control electrode coupled to the corresponding first signal line.

To further achieve the above objects in a whole or in part and in accordance with the purpose of the present invention, as embodied and broadly described, a storage device, comprising a plurality of first signal lines extending along a first direction, a plurality of second signal lines extending along a second direction to cross the first signal lines at prescribed intervals, a plurality of cells corresponding to intersections of the first signal lines and the second signal lines, wherein the cells include a transistor having a gate insulating layer of a gate electrode being a material that has a residual polarization characteristic.

To further achieve the above objects in a whole or in part and in accordance with the purpose of the present invention, as embodied and broadly described, a storage device, comprising a plurality of first signal lines extending along a first direction, a plurality of second signal line pairs extending along a second direction to cross the first signal lines at prescribed intervals, a storage cell coupled at a corresponding intersection of the first signal lines and the pairs of second signal lines, wherein the storage cell comprises, a first transistor coupled between each pair of the second signal line pairs having a second electrode coupled to a first reference voltage, a second transistor having a second electrode coupled to one of the second signal line pairs, a first electrode coupled to a first electrode of the first transistor, and a control electrode coupled to a corresponding first signal line, and a third transistor having a second electrode coupled to the other one of the second signal line pairs, a first electrode coupled to a control electrode of the first transistor, and a control electrode coupled to the corresponding first signal line.

To further achieve the above objects in a whole or in part and in accordance with the purpose of the present invention, as embodied and broadly described, a nonvolatile ferroelectric memory, comprising a semiconductor substrate, an insulating layer that divides the substrate into first, second and third regions, a first gate electrode over a ferroelectric material over the first region of the substrate, a second and a third gate electrodes over second and third gate insulating films that are respectively over the second and third regions of the substrate on opposite sides of the first gate electrode, first source/drain regions in the first region of the substrate on both sides of the first gate electrode, and second and third source/drain regions in the respective second and third regions of the substrate on both sides of the second and third gate electrodes.

To further achieve the above objects in a whole or in part and in accordance with the purpose of the present invention, as embodied and broadly described, a semiconductor memory device, comprising a semiconductor substrate, a first gate electrode on a first gate insulating film over a first region of the substrate, a second gate electrode and a third gate electrode over second and third regions of the substrate, respectively, each with a gate insulating film disposed therebetween, first source/drain regions in the first region of the substrate on both sides of the first gate electrode, second and third source/drain regions on both sides of the second and third gate electrodes in the second and third regions of the substrate, respectively, a first interconnection layer that provides a first reference voltage to the first drain region, a second interconnection layer that electrically couples the first source region to the second source region, and a third interconnection layer that electrically couples the first gate electrode and the third source region.

To further achieve the above objects in a whole or in part and in accordance with the purpose of the present invention, as embodied and broadly described, a method for fabricating a nonvolatile ferroelectric memory, comprising forming a semiconductor substrate, forming a first gate electrode over a ferroelectric gate insulating film disposed over a first region of the substrate, forming a second gate electrode and a third gate electrode over second and third regions of the substrate, respectively, each with a gate insulating film disposed therebetween, forming first source/drain regions in the first region of the substrate on both sides of the first gate electrode, and forming second and third source/drain regions on both sides of the second and third gate electrodes in the second and third regions of the substrate, respectively.

It is to be understood that both the foregoing general description and the following detailed description are exemplary and explanatory and are intended to provide further explanation of the invention as claimed.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

The invention will be described in detail with reference to the following drawings in which like reference numerals refer to like elements wherein.

DETAILED DESCRIPTION OF PREFERRED EMBODIMENTS

Figure 1:
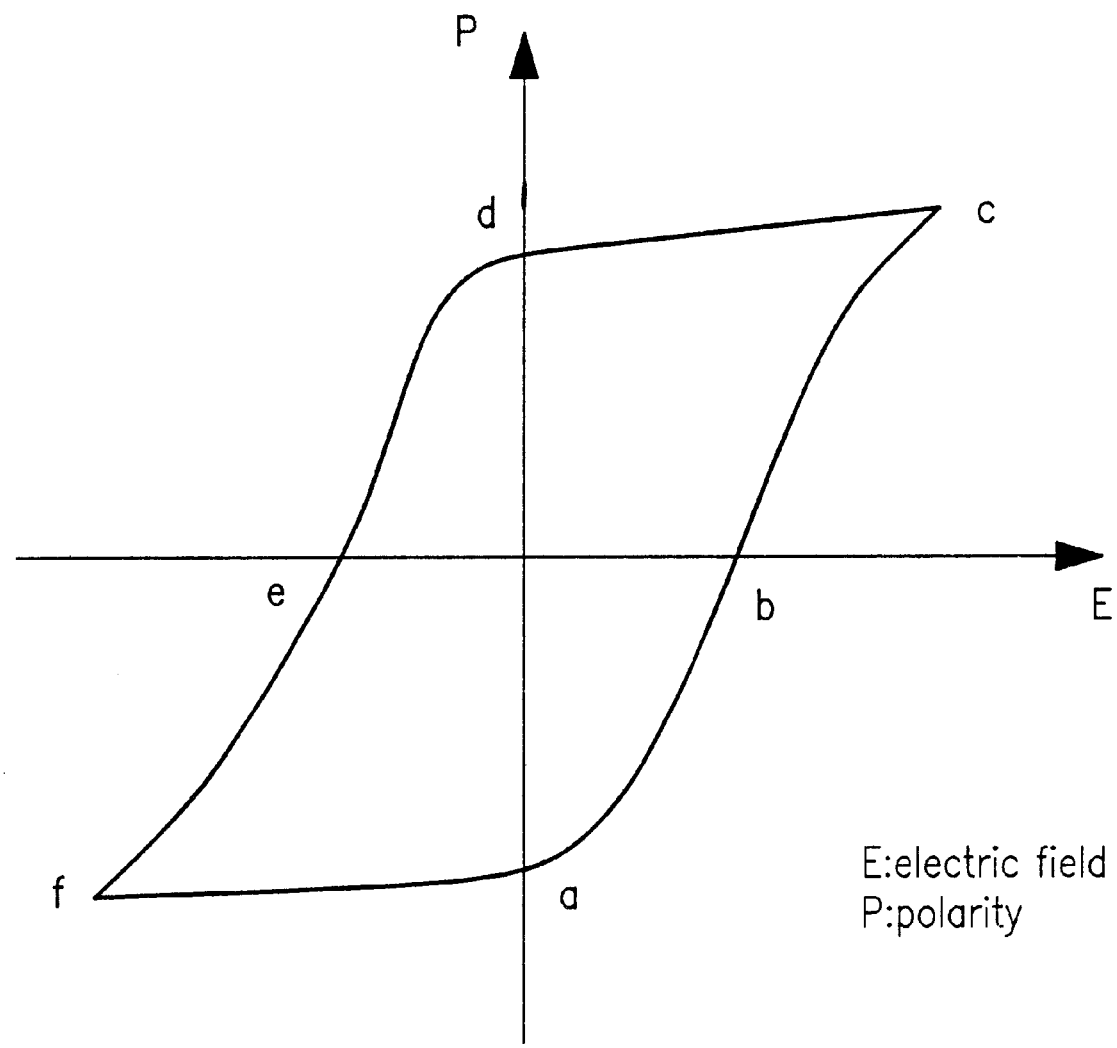
FIG. 1 illustrates a characteristic curve of a hysteresis loop of a ferroelectric material.
Figure 2:
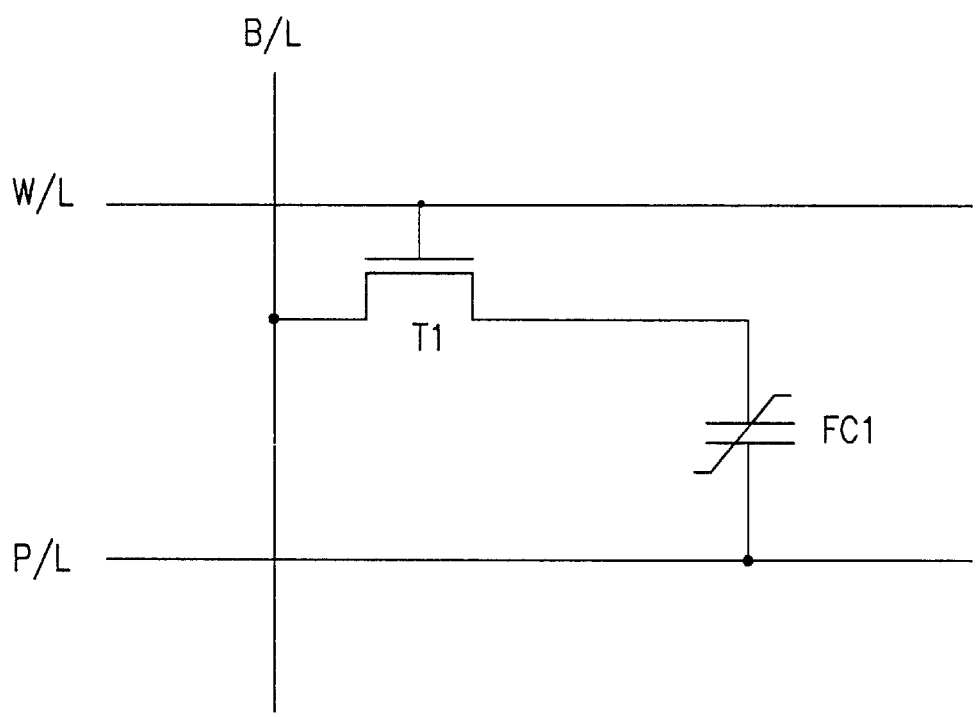
FIG. 2 is a schematic diagram that illustrates a system of unit cell of a related art non-volatile ferroelectric memory.
Figure 3A:
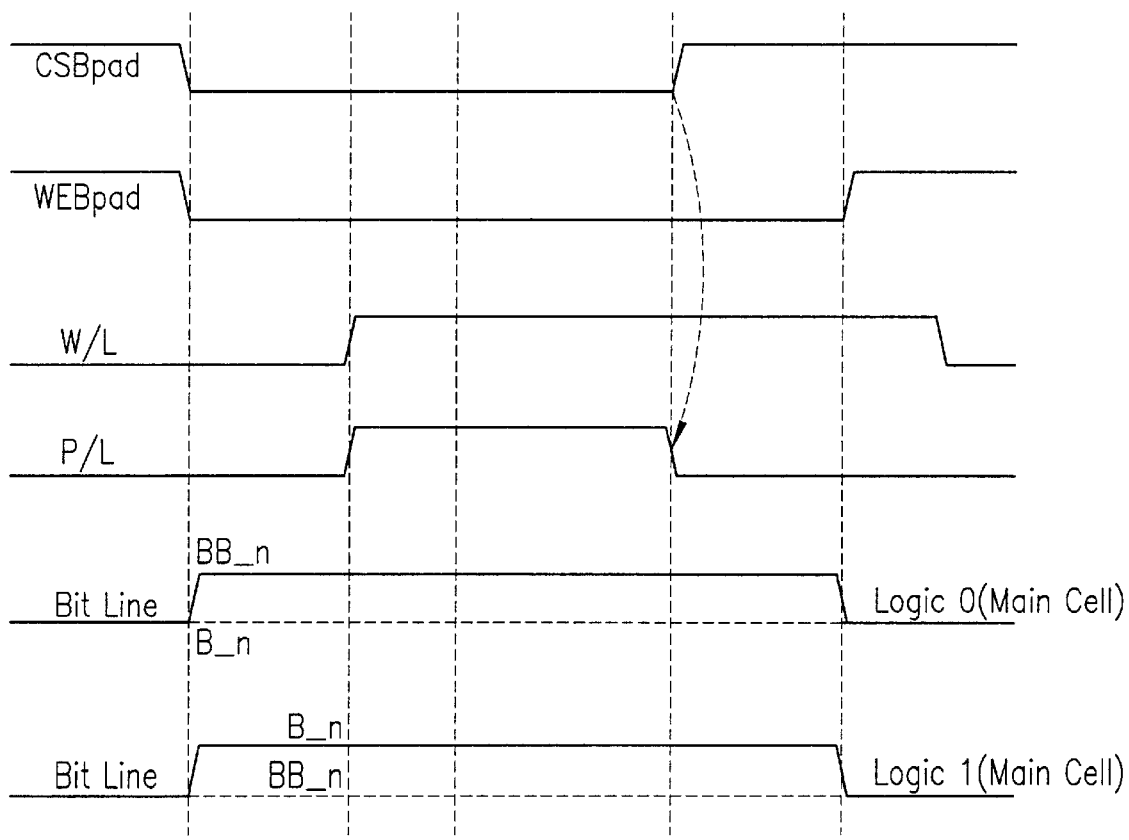
FIG. 3A illustrates a timing diagram of a write mode operation of the related art nonvolatile ferroelectric memory.
Figure 3B:
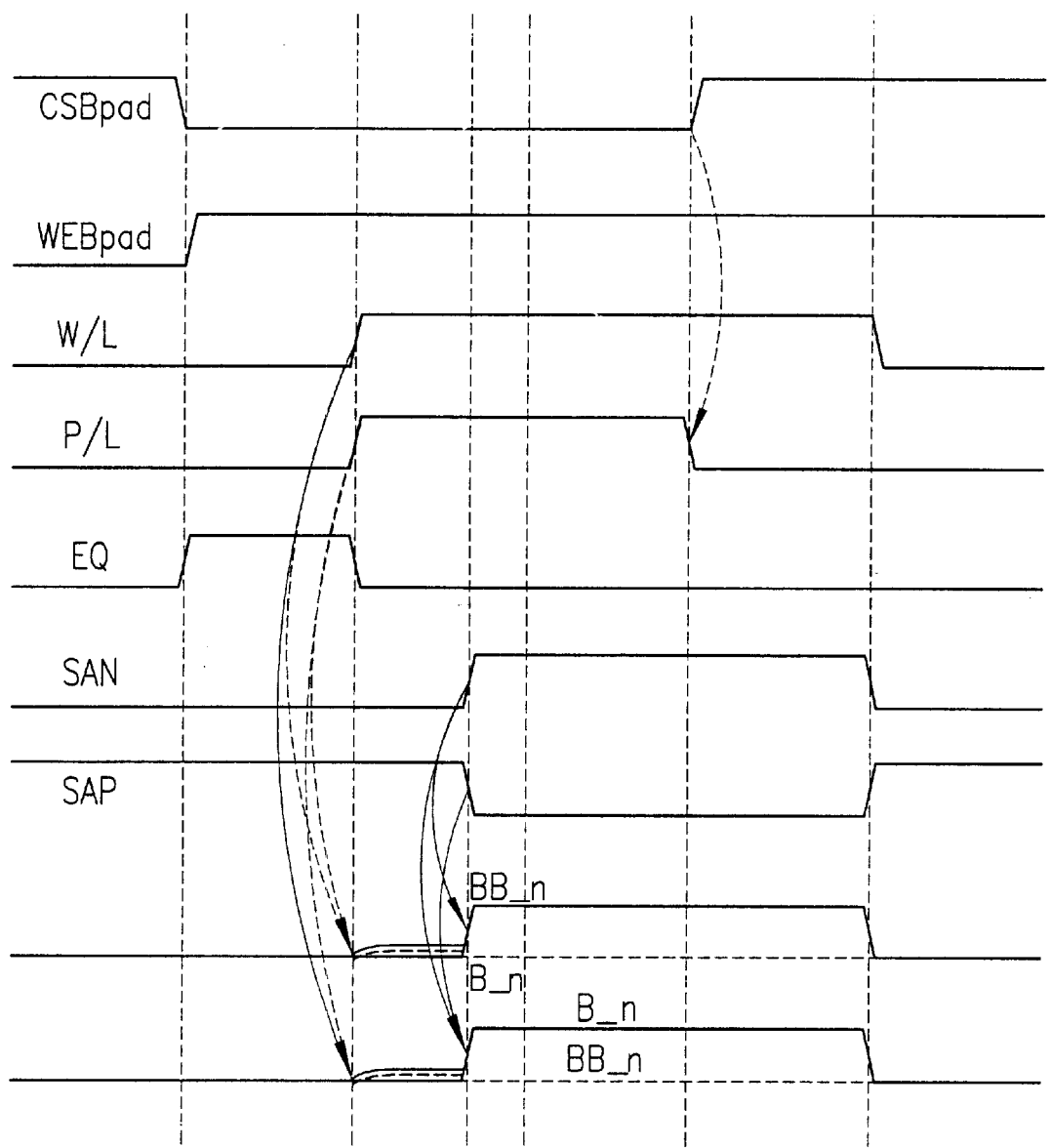
FIG. 3B illustrates a timing diagram of a read mode operation of the related art nonvolatile ferroelectric memory.
Figure 4:
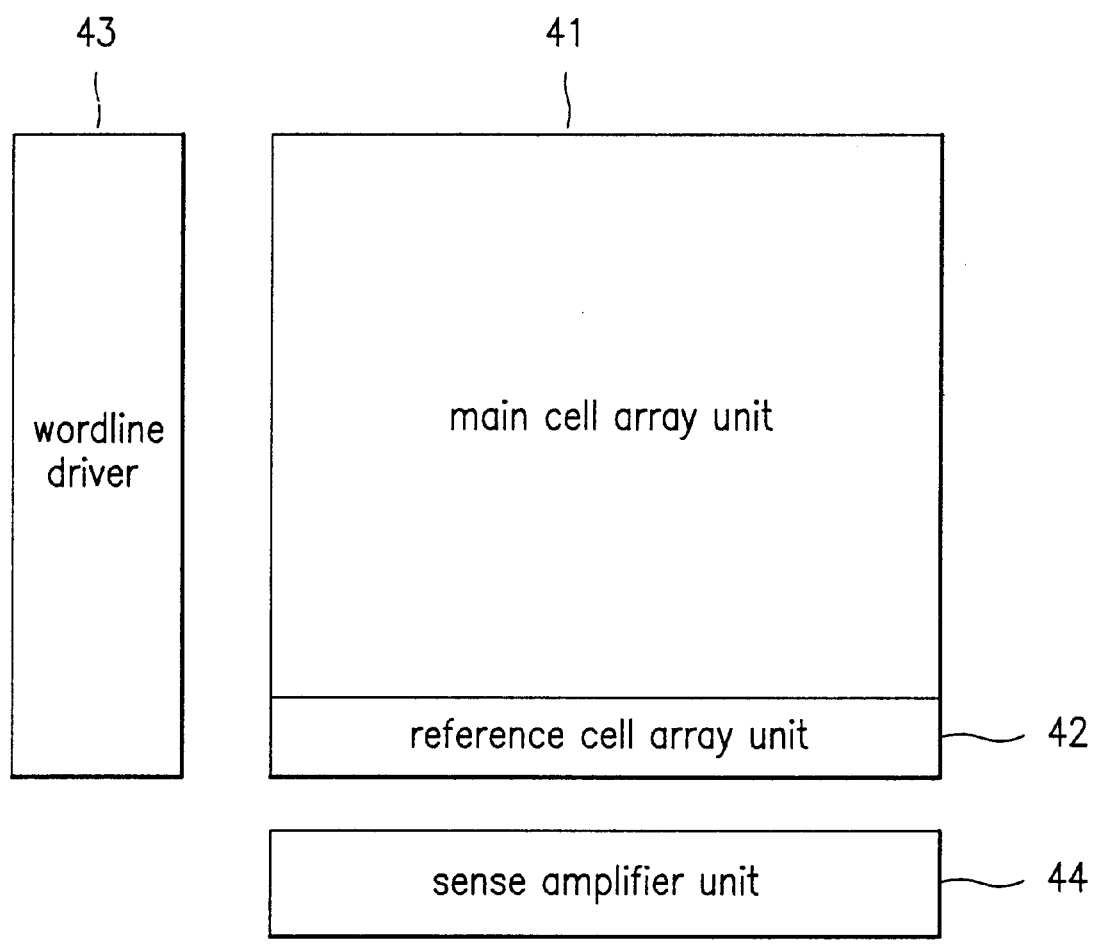
FIG. 4 illustrates a block diagram of a related art nonvolatile ferroelectric memory.
Figure 5:
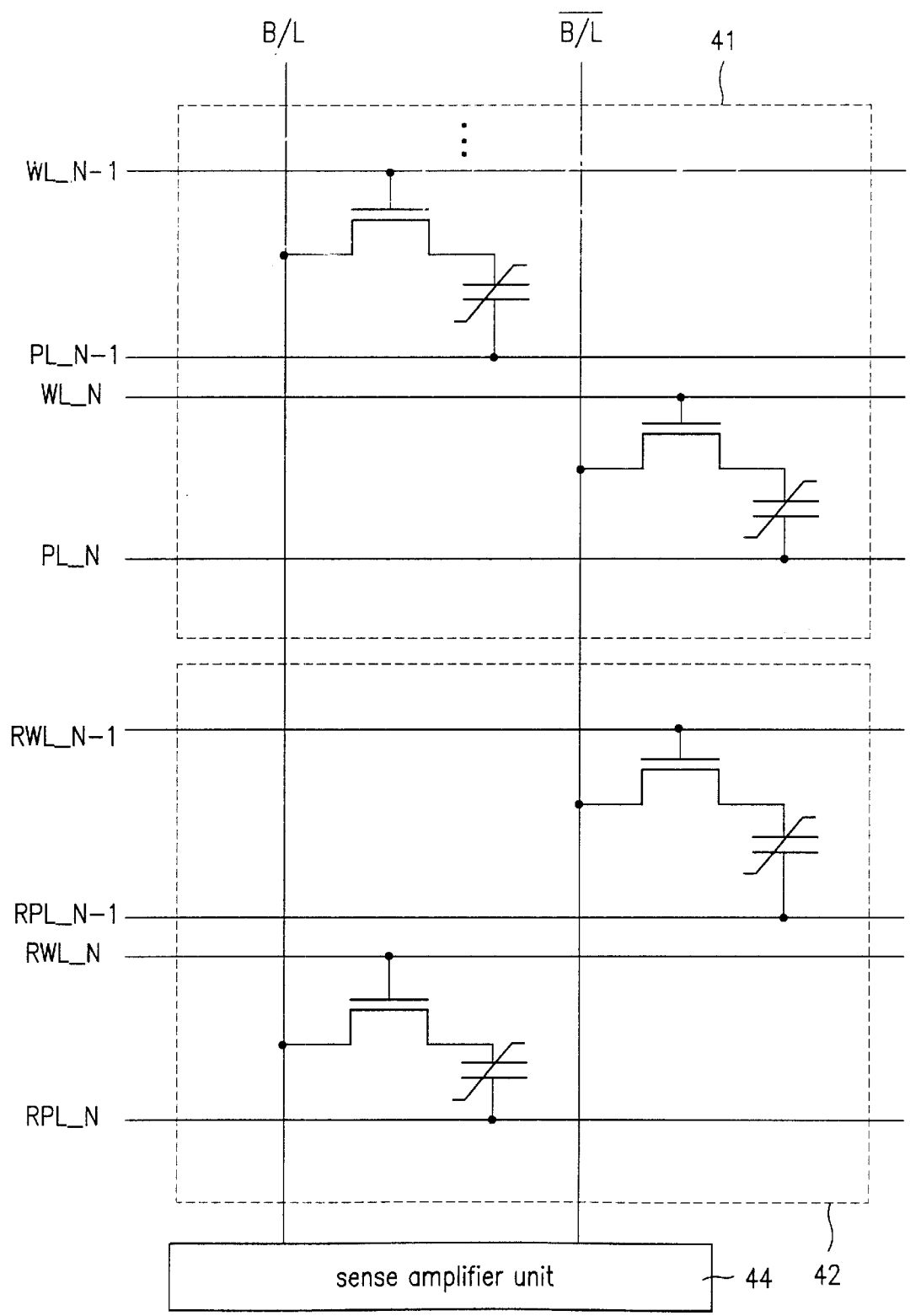
FIG. 5 illustrates a partially detailed view of a cell array of the related art nonvolatile ferroelectric memory of FIG. 4.
Figure 6:
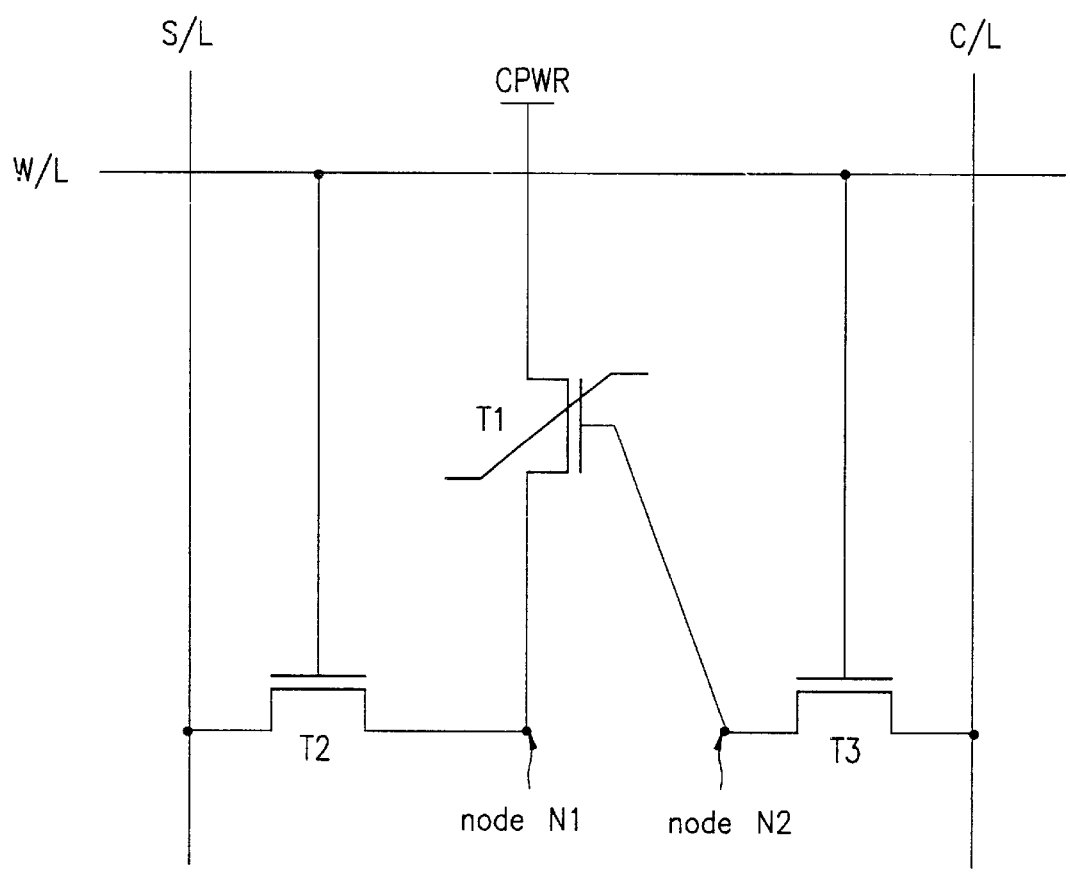
FIG. 6 is a diagram that illustrates a preferred embodiment of a system of unit cell of a non-volatile ferroelectric memory in accordance with the present invention.

FIG. 6 is a diagram that illustrates a preferred embodiment of a unit cell of a non-volatile ferroelectric memory in accordance with the present invention. As shown in FIG. 6, the preferred embodiment of the unit cell of a non-volatile ferroelectric memory in accordance with the present invention includes a wordline W/L formed in a row direction, a sensing line SL and a control line CL formed in a column direction spaced a distance from each other and a first transistor T1 having a drain coupled to a power source voltage and using a ferroelectric material as a gate dielectric material. A second transistor T2 has a drain coupled to the sensing line, a source coupled to a source of the first transistor T1, and a gate coupled to the wordline. A third transistor T3 has a drain coupled to the control line, a source coupled to a gate of the first transistor T1, and a gate coupled to the wordline. The first transistor T1 is preferably a ferroelectric NMOS transistor having a gate insulating film formed of a ferroelectric material, and the second and third transistors T2 and T3 are preferably NMOS transistors each having a gate insulating film formed of general gate insulating material.

Operations of the preferred embodiment of the unit cell of a nonvolatile ferroelectric memory will now be described. In a write mode, when the wordline is enabled from low to high, the second and third transistors T2 and T3 are enabled. In this instance, a critical voltage higher than polarization inversion of a ferroelectric material is applied between the sensing line SL and the control line CL to provide the critical voltage to a node N1, which is the source of the second transistor T2, and to a node N2, which is the source of the third transistor T3. The voltage provided to the node N1 is provided to the source of the first transistor T1 and the substrate, and the voltage provided to the node N2 is provided to the gate of the first transistor T1. Accordingly, a polarization direction of the ferroelectric material of the first transistor T1 is fixed by voltages of the gate and the substrate. When the voltage of the substrate is higher than the voltage of the gate, a logic zero, i.e., "0" is stored, and when the voltage of the substrate is lower than the voltage of the gate, a logic high, i.e., "1" is stored.

Figure 7A:
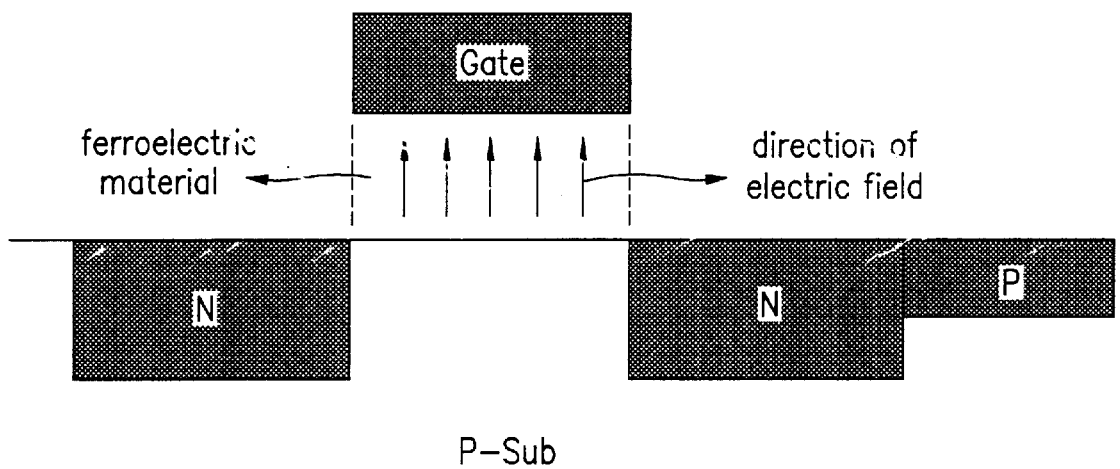
FIGS. 7A and 7B are diagrams that illustrate storage states of logic "0" and logic "1", respectively.
Figure 7B:
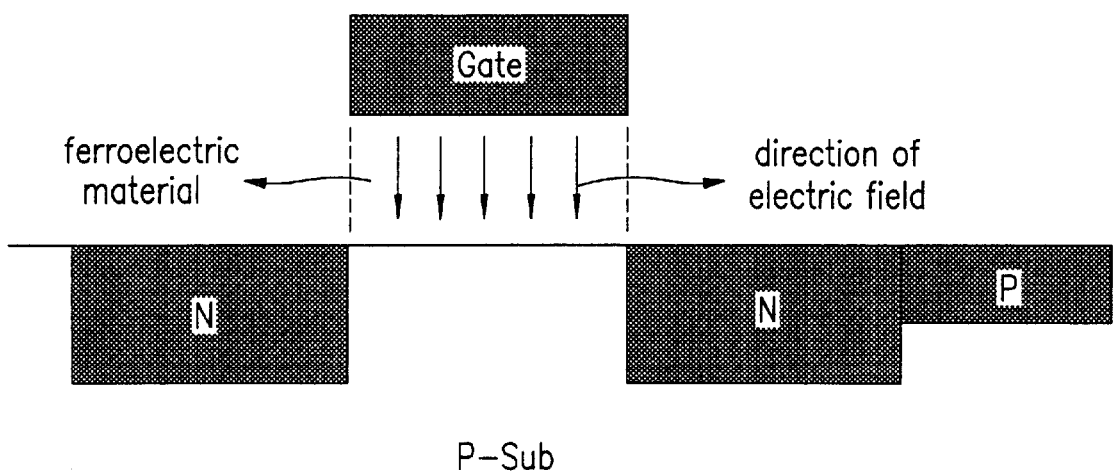
Figure 8A:
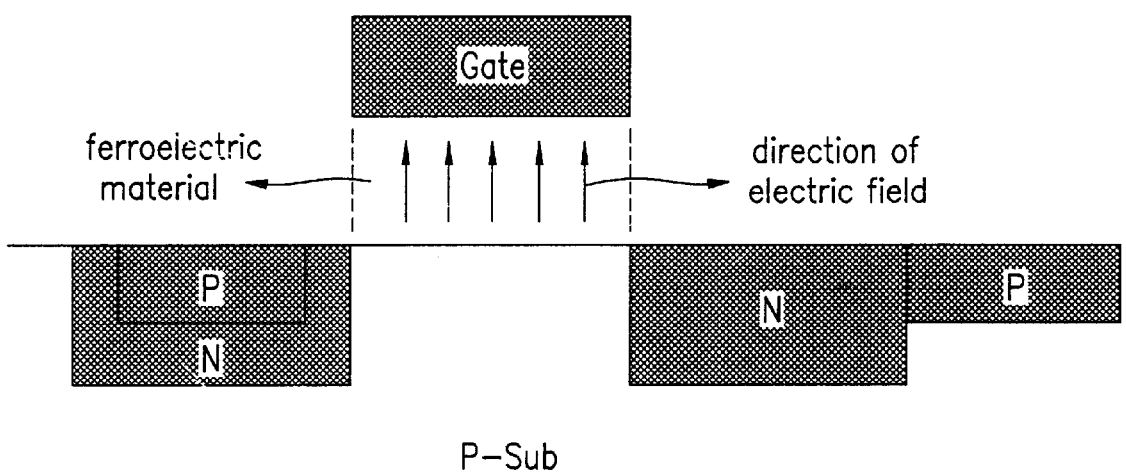
FIGS. 8A and 8B are diagrams that illustrate storage states of logic "0" and logic "1", respectively.
Figure 8B:
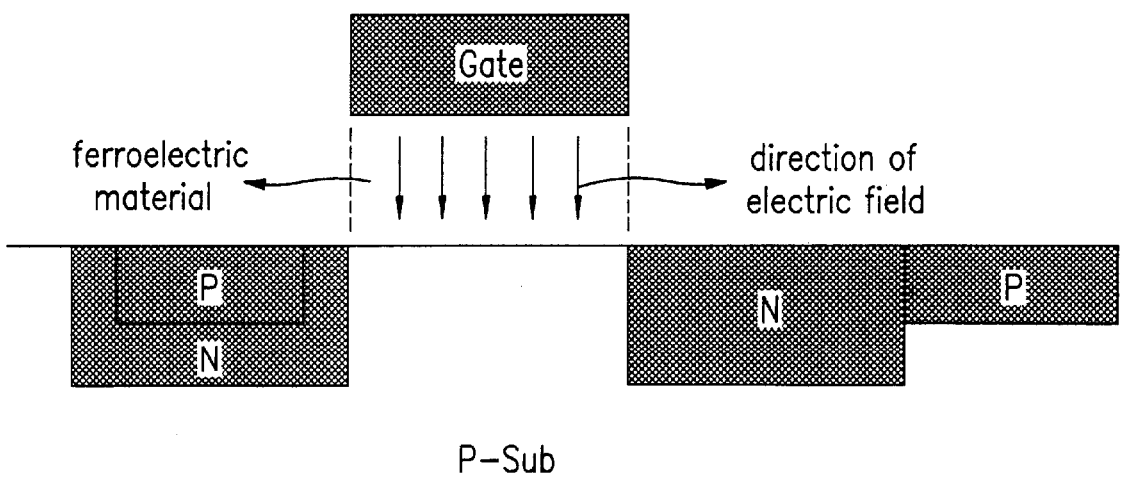

FIGS. 7A and 7B, and FIGS. 8A and 8B are diagrams that respectively illustrate preferred embodiments showing logic "0" storage states and logic "1" storage states. FIGS. 7A and 8A illustrate logic "0" storage states, and FIGS. 7B and 8B illustrate logic "1" storage states.

In a read mode, after the wordline is enabled from low to high in a state a power source voltage in a range of 1/2 Vcc is kept applied to the drain of the first transistor, the sensing line SL and the control line CL are pulled-down and equalized to a ground level, a preset level or the like, respectively. To load a reference voltage on the control line, the control line is coupled to a reference level generating circuit (not shown) and a reference cell (not shown). Therefore, as a current to the first transistor T1 is varied with a polarity of the first transistor T1, voltage levels of the sensing line and the control line become different. The voltage levels of the sensing line and the control line are amplified and forwarded by the sensing amplifier. That is, when a logic "0" is stored on the first transistor T1, a level of the sensing line is lower than a level of the control line, and when a logic "1" is stored in the first transistor T1, a level of the sensing line is higher than a level of the control line.

Figure 9:
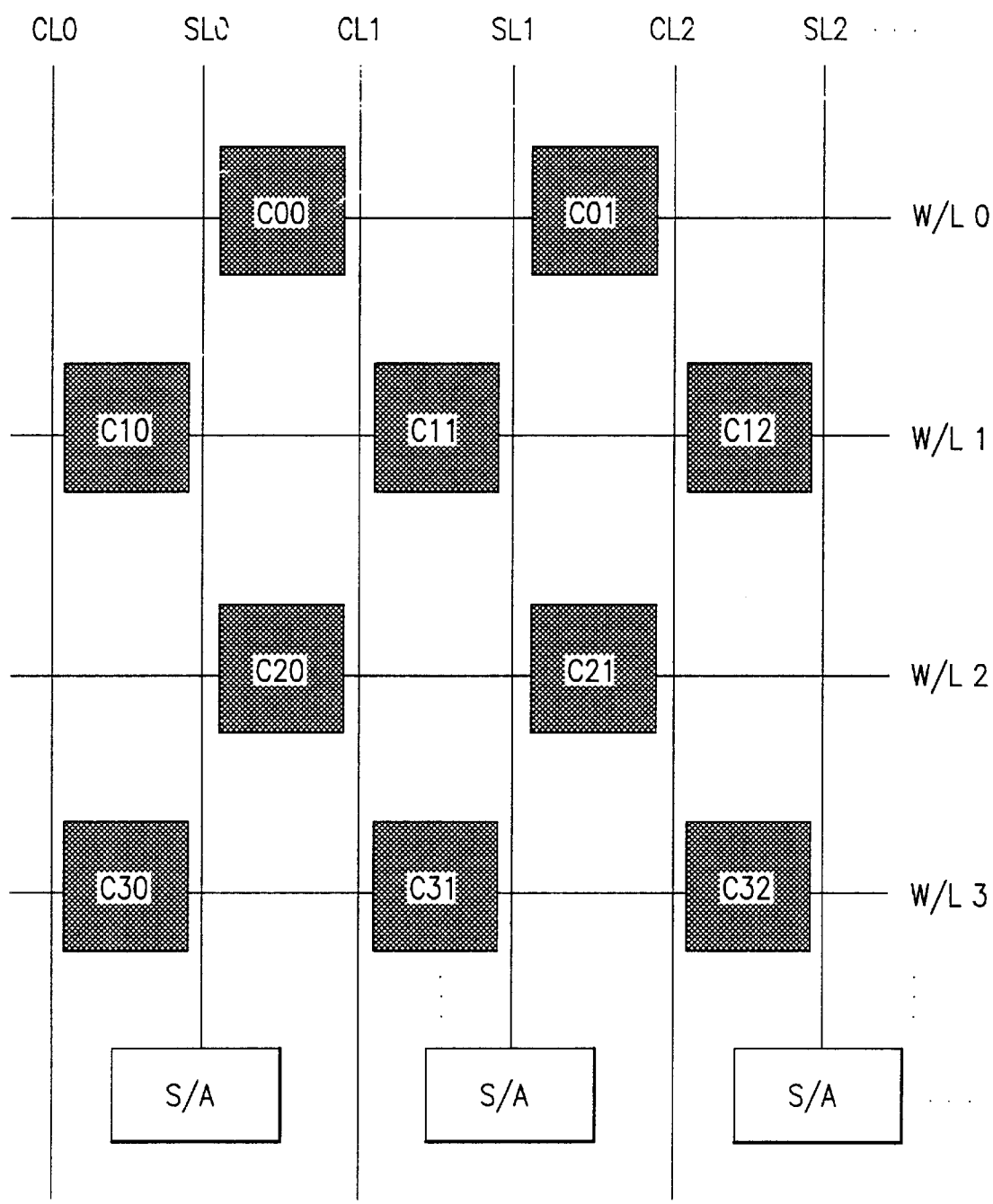
FIG. 9 is a diagram that illustrates a preferred embodiment of a nonvolatile ferroelectric memory in accordance with the present invention.

FIG. 9 is a diagram that illustrates a preferred embodiment of a nonvolatile ferroelectric memory in accordance with the present invention. As shown in FIG. 9, cells of the nonvolatile ferroelectric memory are arranged in a folded form. The control line and the sensing line form one pair to provide a plurality of control line and sensing line pairs. Every sensing line has a sensing amplifier coupled thereto. In addition, the nonvolatile ferroelectric memory includes peripheral circuits such as wordline drivers, decoders and input/output circuitry (not shown) coupled to the cell array.

Figure 10:
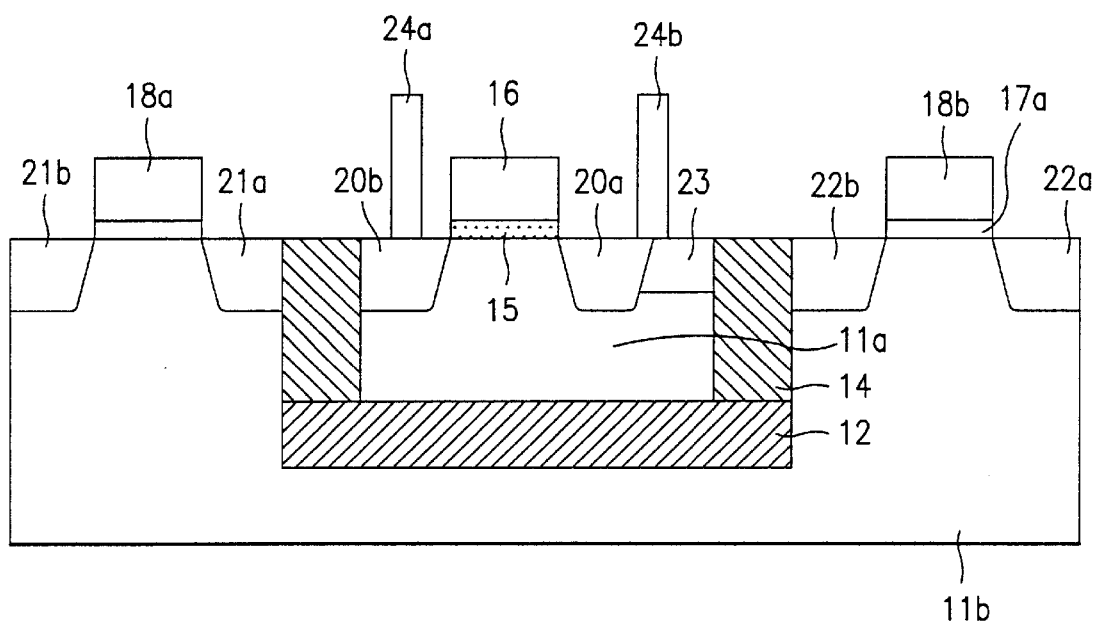
FIG. 10 is a diagram that illustrates a preferred embodiment of a section of a nonvolatile ferroelectric memory in accordance with the present invention.

FIG. 10 is a diagram that illustrates a first preferred embodiment of a section of a nonvolatile ferroelectric memory in accordance with the present invention. As shown in FIG. 10, the nonvolatile ferroelectric memory in accordance with a first preferred embodiment includes a first semiconductor substrate 11a, insulating layers 12 and 14 that surround sides and a bottom of the first semiconductor substrate 11a and a second semiconductor substrate 11b that surrounds the sides and the bottom of the insulating layers. A first gate electrode 16 is over the first semiconductor substrate 11a with a ferroelectric material 15 disposed inbetween and second and third gate electrodes 18a and 18b are formed over the semiconductor substrate 11b on both sides of the insulating layers 12 and 14 each with a gate insulating film 17a disposed inbetween. First source/drain regions 20a/20b of a conduction type opposite to the first semiconductor substrate 11a formed in surfaces of the first semiconductor substrate 11a are on both sides of the first gate electrode 16. Second and third source/drain regions 21a/21b and 22a/22b of a conduction type opposite to the second semiconductor substrate 11b are formed in surfaces of the second semiconductor substrate 11b on both sides of the second and third gate electrodes 18a and 18b. A first impurity region 23 of a conduction type identical to the first semiconductor substrate 11a is in a surface of the first semiconductor substrate 11a on one side of the first source region 20a.

The insulating layers 12 and 14 have a first insulating layer 12 on a bottom of the first semiconductor substrate 11a and a second insulating layer 14 preferably of a trench type at the sides of the first semiconductor substrate 11a to be coupled to ends of the first insulating layer 12. The first insulating layer 12 is preferably formed by implanting impurities of a conduction type opposite to the first semiconductor substrate 11a. Further, there are a first interconnection layer 24a for applying a power source voltage thereto in the first drain region 20b, a second interconnection layer 24b for electrically coupling the first source region 20a and the second source region 21a, and a third interconnection region (not shown) for electrically coupling the first gate electrode 16 and the third source region 22a. A power source voltage in a range of 1/2 Vcc is preferably provided to the first drain region 20b.

The first transistor T1 includes the first gate electrode 16, the first source/drain regions 20a/20b, and the ferroelectric material 15 between the first gate electrode 16 and the first semiconductor substrate 11a. The first semiconductor substrate 11a having the first transistor T1 formed thereon is separated from the second semiconductor substrate 11b completely by the first insulating layer 12 formed by impurity implantation and the trench type second insulating layer 14. Since the first semiconductor substrate 11a, which is an inner substrate of the first transistor T1, is separated from the second semiconductor substrate 11b, which is an outer substrate, by the first insulating layer 12 and the second insulating layer 14, every cell preferably requires a first impurity region 23 of a conduction type opposite to the first semiconductor substrate 11a additionally for controlling a bias of the first semiconductor substrate 11a. A CPWR terminal (e.g., an external power source voltage) is coupled to the first drain region 20b. Therefore, when a high voltage is provided to the first semiconductor substrate 11a (e.g., the node N1 shown in FIG. 6), the second semiconductor substrate 11b is separated from the high voltage by the first and second insulating layers. At the end, the gate of the first transistor T1 is coupled to the node N2 and the source is coupled to the node N1 as shown in FIG. 6. Accordingly, a bias of the first semiconductor substrate 11a, the inner substrate, is adjusted by the node N1.

A first preferred embodiment of a method for fabricating a nonvolatile ferroelectric memory in accordance with the present invention will now be described. FIGS. 11A~11E are diagrams that illustrate cross-sections showing the first preferred embodiment of the a method for fabricating a nonvolatile ferroelectric memory. The first preferred embodiment of a method for fabricating a memory can be used, for example, to fabricate the nonvolatile ferroelectric memory of FIG. 10.

Figure 11A:
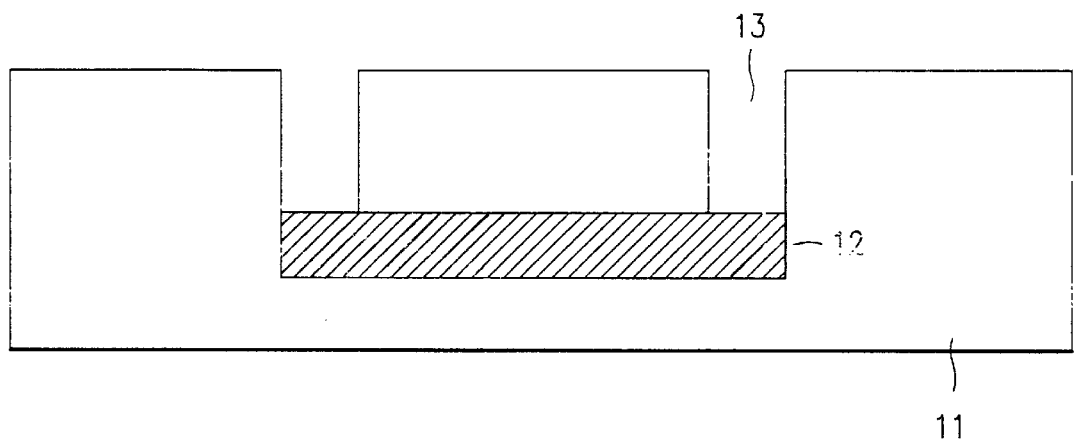
FIGS. 11A–11E are diagrams that illustrate cross-sections showing a method for fabricating a nonvolatile ferroelectric memory in accordance with a preferred embodiment of the present invention.
Figure 11B:
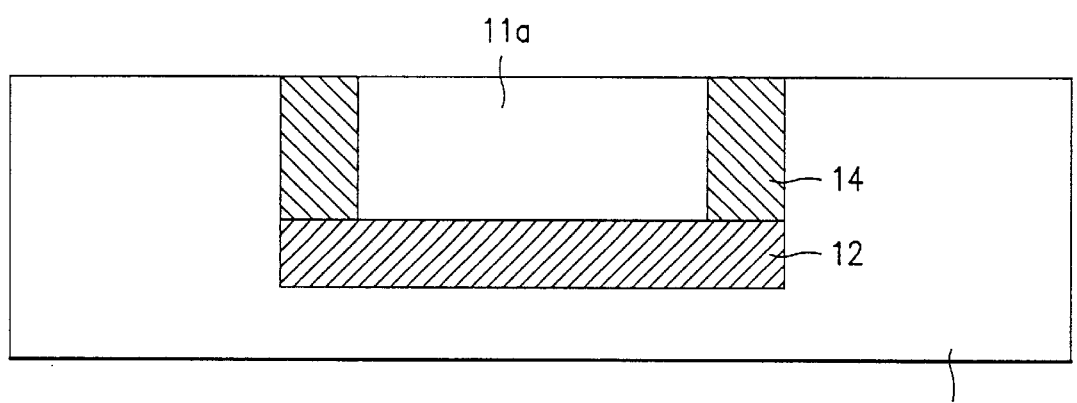

As shown in FIG. 11A, a first insulating layer 12 is formed at a required depth of the first conduction type semiconductor substrate 11 preferably by impurity ion implanting. Then, the semiconductor substrate 11 is etched to a required depth to form a trench 13 such that the trench is coupled to ends of the first insulating layer 12. As shown in FIG. 11B, an insulating material is stuffed in the trench 13 to form a second insulating layer 14 and electrically separate the first conduction type semiconductor substrate 11 by the first insulating layer 12 and the second insulating layer 14. In the following description, the semiconductor substrate inside of the first insulating layer 12 and the second insulating layer 14 is defined as a first semiconductor substrate 11a and the semiconductor substrate outside of the first and second insulating layers 12 and 14 is defined as a second semiconductor substrate 11b.

Figure 11C:
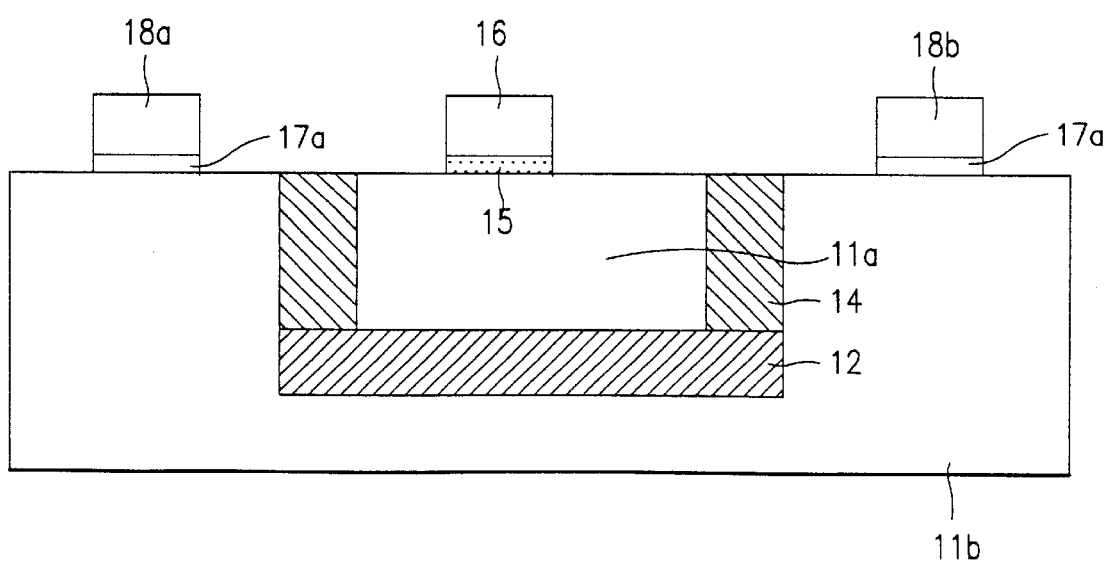

As shown in FIG. 11C, a first gate electrode 16 is formed over the first semiconductor substrate 11a with a ferroelectric material 15 disposed inbetween, and a second and a third gate electrodes 18a and 18b are formed over the second semiconductor substrate 11b on both sides of the first semiconductor substrate 11a. Each of the second and third gate electrodes has a general gate insulating material 17a disposed inbetween.

Figure 11D:
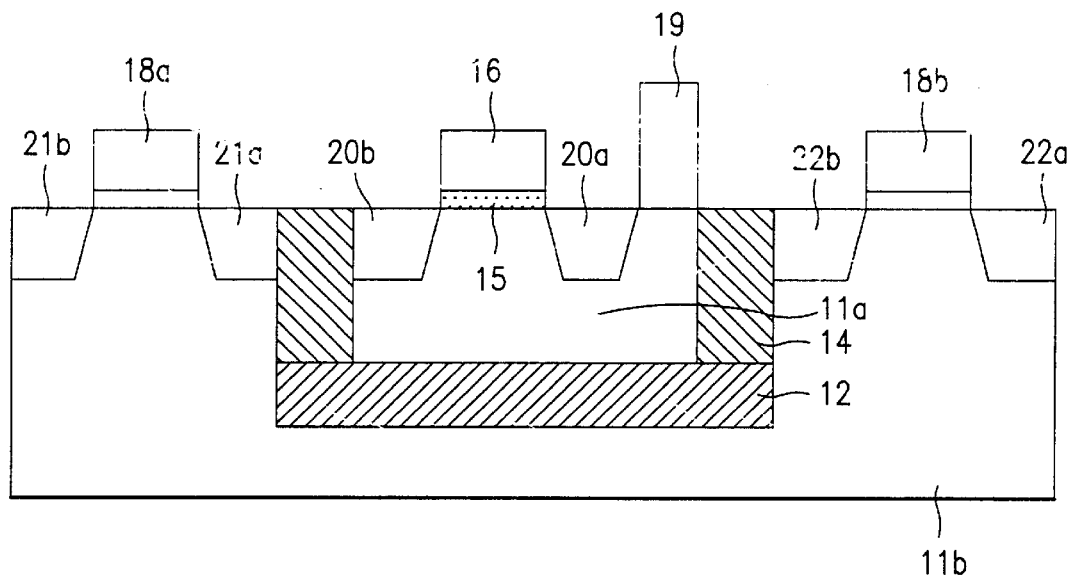

As shown in FIG. 11D, a portion of the first semiconductor substrate 11a in which a source region is to be formed on one side of the first gate electrode 16 is masked with a masking material 19 and implanted with impurities of a conduction type opposite to the first and second semiconductor substrates 11a and 11b. Accordingly, first source/drain regions 20a/20b are formed in surfaces of the first semiconductor substrate 11 a on both sides of the first gate electrode 16, second source/drain regions 21a/21b are formed in surfaces of the second semiconductor substrate 11b on both sides of the second gate electrode 18a, and third source/drain regions 22a/22b are formed in surfaces of the second semiconductor substrate 11b on both sides of the third gate electrode 18b.

Figure 11E:
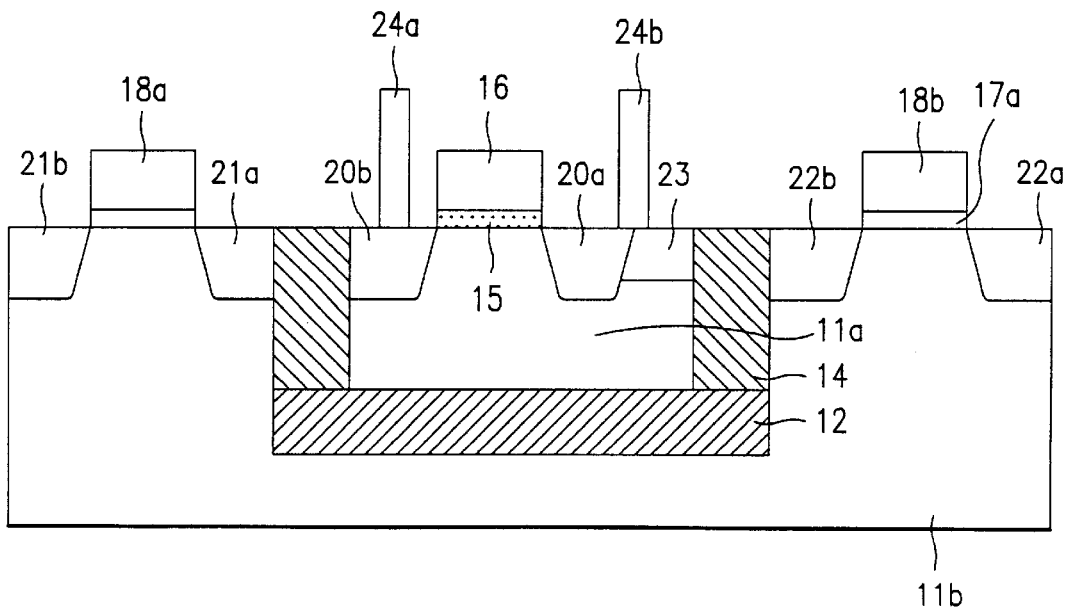

After the mask material 19 is removed as shown in FIG. 11E, ions are selectively implanted to form a first impurity region 23 of a conduction type identical to the first semiconductor substrate 11a. In one instance, the first and second semiconductor substrate 11a and 11b are P conduction type, and the source/drain regions are of an N conduction type. Then, a first interconnection layer 24a for providing the power source voltage to the first drain region 20b is formed, and a second interconnection layer 24b for electrically coupling the first source region 20a to the second source region 21a is formed. In addition although not shown, a third interconnection layer (not shown) is formed electrically coupling the first gate electrode 16 and the third source region 22a.

Figure 12:
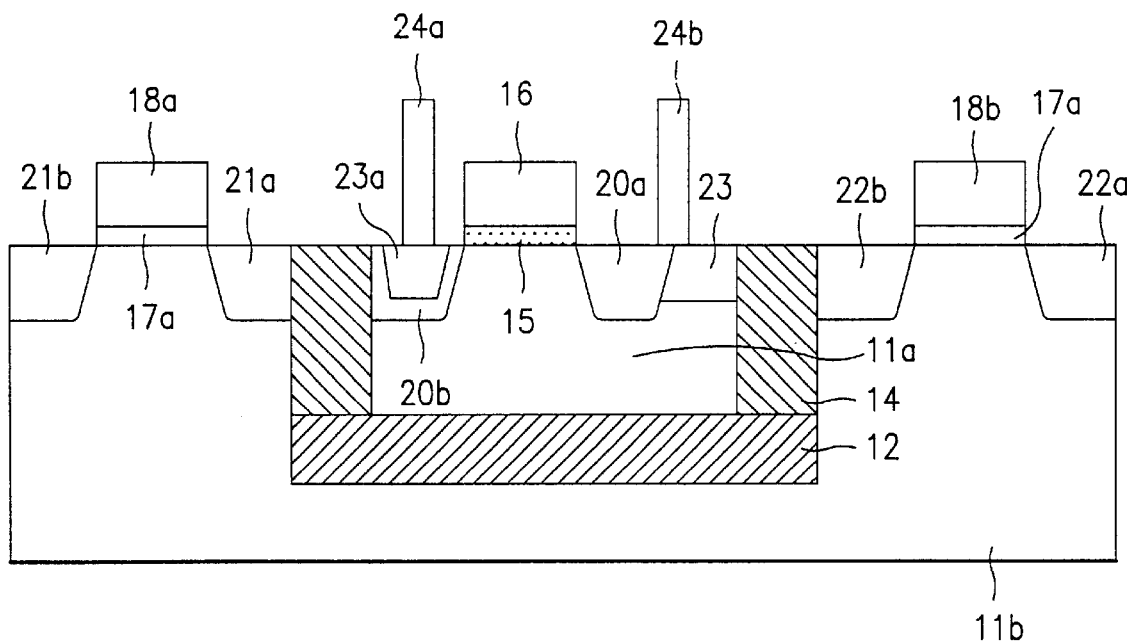
FIG. 12 is a diagram that illustrates another preferred embodiment of a cross-section of a nonvolatile ferroelectric memory in accordance with the present invention.

FIG. 12 is a diagram that illustrates a second preferred embodiment of a section of a nonvolatile ferroelectric memory in accordance with the present invention. As shown in FIG. 12, the nonvolatile ferroelectric memory in accordance with the second preferred embodiment has a sectional structure similar to the first preferred embodiment of the nonvolatile ferroelectric memory with a feature of a second impurity region 23a of a conduction type identical to the first semiconductor substrate 11a is formed in the first drain region 20b. In this instance, preferably a power source voltage 1/2 Vcc is provided to the second impurity region 23a. Since the second impurity region 23a and the first drain region 20b form a PN diode, the power source voltage provided to the second impurity region 23a is provided to the first semiconductor substrate 11a, but not to the second semiconductor substrate 11b, which is preferably at a ground level because of the first and second insulating layers 12 and 14. Thus, even if a high voltage is induced to the first semiconductor substrate 11a, the high voltage is not provided to the second impurity region 23a because of the first drain region 20b. Therefore, the voltage induced to the first semiconductor substrate 11a and the power source voltage are separated from each other.

A preferred embodiment of a method for fabricating a nonvolatile ferroelectric memory in accordance with the present invention will now be described. FIGS. 13A~13E are diagrams that illustrate cross-sections showing the second preferred embodiment of the method for fabricating a nonvolatile ferroelectric memory. The second preferred embodiment of a method for fabricating a nonvolatile ferroelectric memory can be used, for example, to fabricate the memory of FIG. 12. As the steps of FIGS. 13A~13D are similar to FIGS. 11A~11D, a detailed description will be omitted here.

Figure 13A:
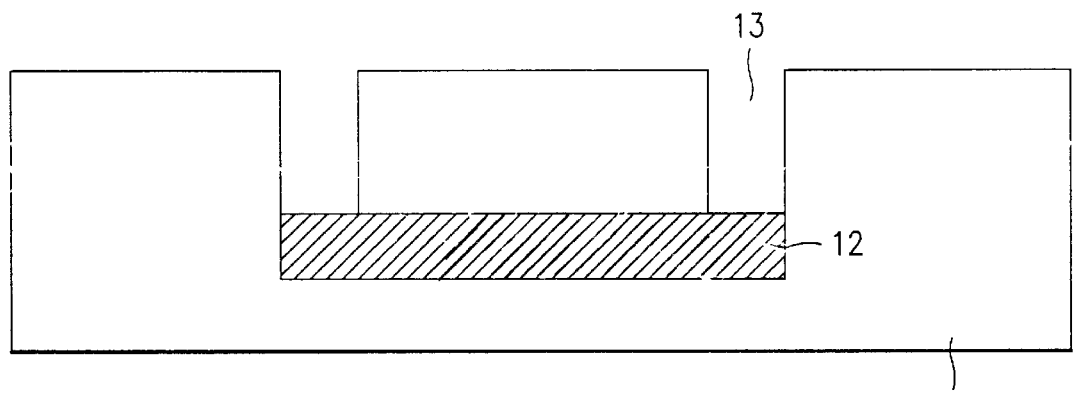
FIGS. 13A~13E are diagrams that illustrate sections showing a method for fabricating a nonvolatile ferroelectric memory in accordance with another preferred embodiment of the present invention.
Figure 13B:
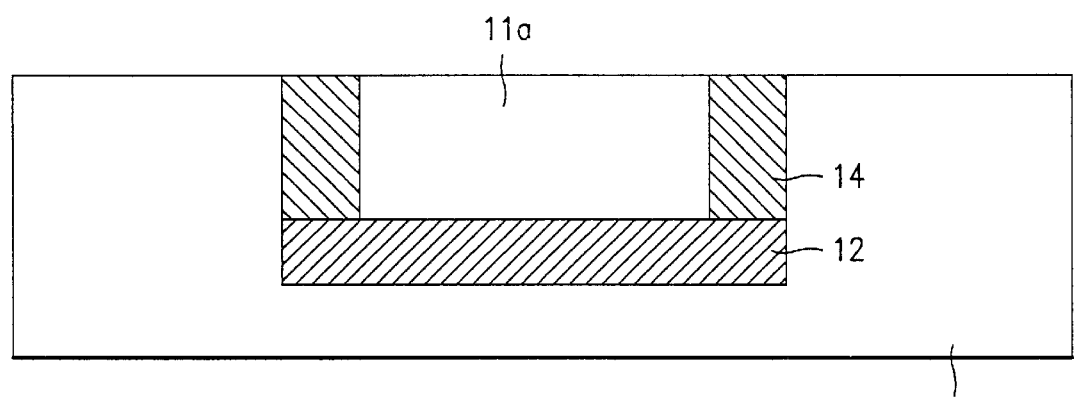
Figure 13C:
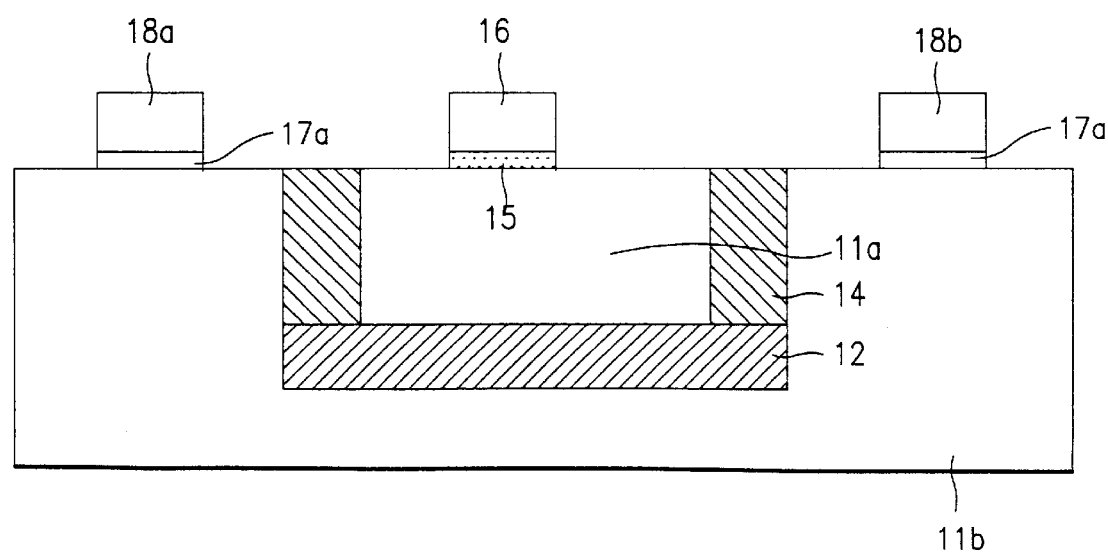
Figure 13D:
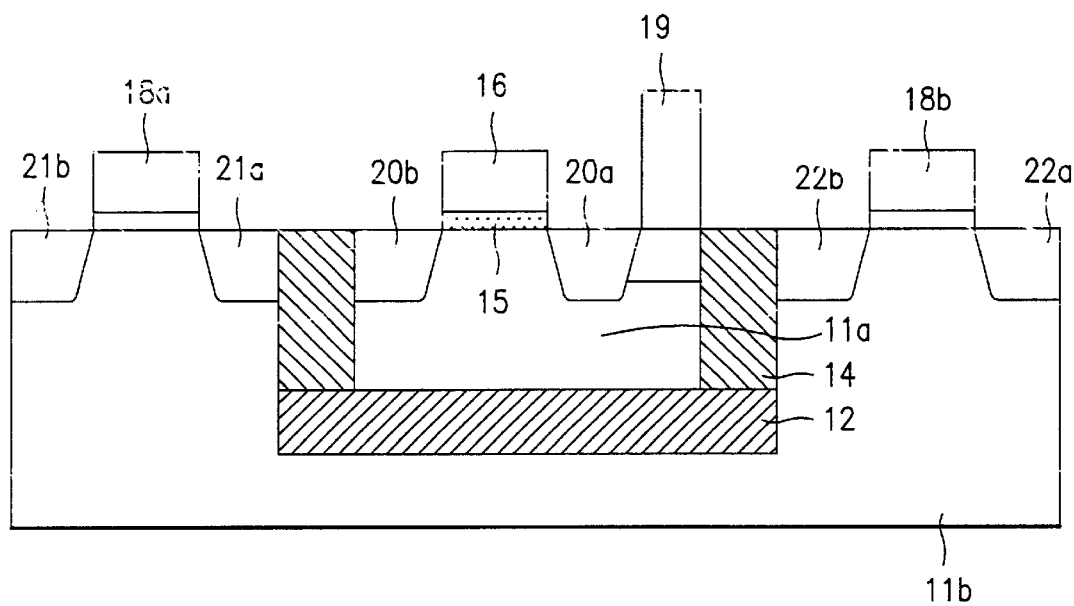
Figure 13E:
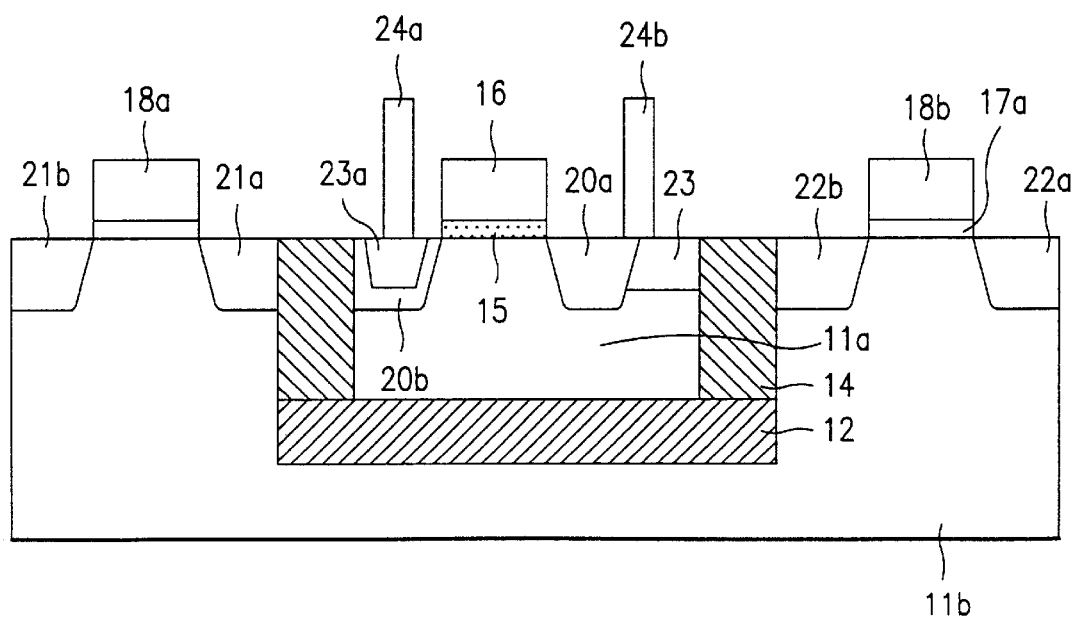

As shown in FIG. 13D, after formation of the first and second source/drain regions 20a/20b, 21a/21b, and the third source/drain regions 22a/22b, a mask material 19 is removed. As shown in FIG. 13E, after masking is made to expose the first drain region 20b and the region having the masking material 19 removed therefrom, impurity ions are implanted to form a first impurity region 23 and the second impurity region 23a of a conduction type identical to the first semiconductor substrate 11a. Then, the first interconnection layer 24a is formed for providing the power source voltage to the second impurity region 23a, and a second interconnection layer 24b is formed for electrically coupling the first source region 20a and the second source region 21a. Though not shown in FIG. 13E, a third interconnection layer is formed for electrically coupling the first gate electrode 16 and the third source regions 22a.

Figure 14:
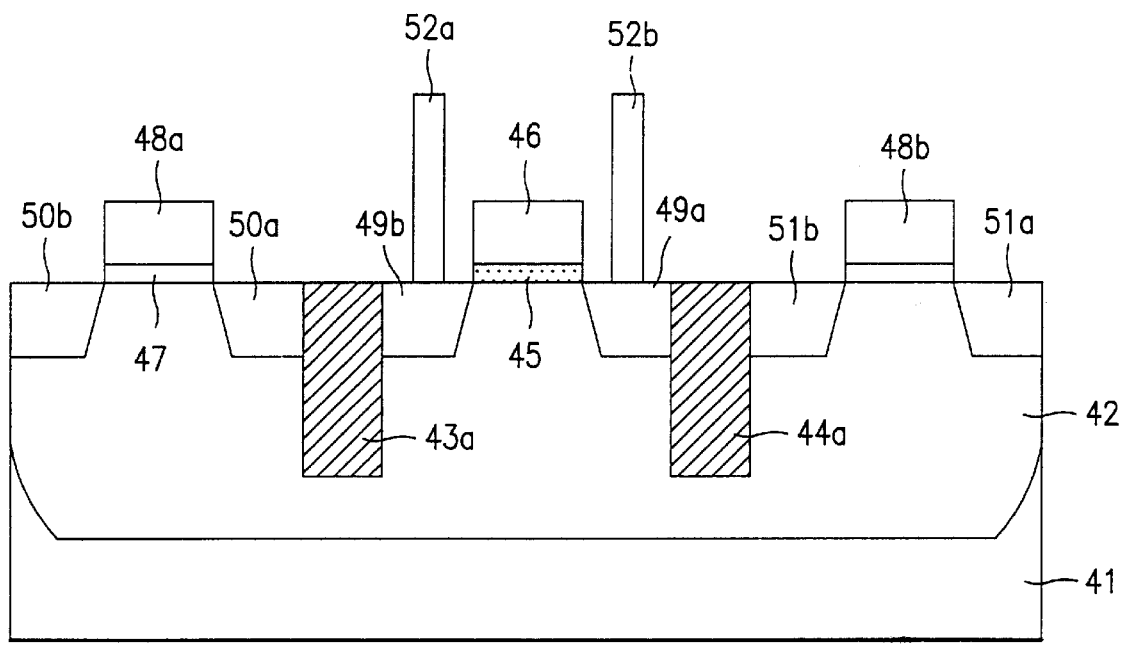
FIG. 14 is a diagram that illustrates another preferred embodiment of a cross-section of a nonvolatile ferroelectric memory in accordance with the present invention.

FIG. 14 is a diagram that illustrates a third preferred embodiment of a section of a nonvolatile ferroelectric memory in accordance with the present invention. As shown in FIG. 14, the nonvolatile ferroelectric memory in accordance with the third preferred embodiment of the present invention includes a first conduction type semiconductor substrate 41, a first conduction type well region 42 in a surface of the first conduction type semiconductor substrate 41 down to a prescribed depth and first and second insulating layers 43a and 44a each for separating the first conduction type well region 42 in a vertical direction at fixed intervals. A first gate electrode 46 is over the first conduction type well region 42 between the first insulating layer 43a and the second insulating layer 44a with a ferroelectric material 45 disposed inbetween. Second and third gate electrodes 48a and 48b are over other outside well regions separated by the first and second insulating layers 43a and 44a on both sides of the first conduction type well region 42 having the first gate electrode 46 thereon, each with a gate insulating film 47 disposed inbetween. First source/drain regions 49a/49b are in the first conduction type well region 42 on both sides of the first gate electrode 46, and second and third source/drain regions 50a/50b and 51a/51b are in the well region 42 on both sides of the second and third gate electrodes 48a and 48b, respectively.

A first interconnection layer 52a is on the first drain region 49b and a second interconnection layer 52b is for electrically coupling the first source region 49a and the second source region 50a. A third interconnection layer (not shown) is for electrically coupling the first gate electrode 46 and the third source region 51a. The first and second insulating layer 43a and 44a are preferably a trench type. In the third preferred embodiment, the first, second and third transistors T1–T3 have identical structures. Although the impurity region 23 of a conduction type identical to the first semiconductor substrate 11a is in every cell for adjusting a bias of the first semiconductor substrate 11a in the first and second preferred embodiments, the impurity region 23 is not in the third preferred embodiment. However, the gate electrode of the first transistor T1 has a gate dielectric film of a ferroelectric material, while the gate electrodes of the second and third transistors T2 and T3 have conventional gate insulating films as shown in FIG. 14.

A third preferred embodiment of a method for fabricating a nonvolatile ferroelectric memory in accordance with the present invention will now be described. FIGS. 15A–15D are diagrams that illustrate cross-sections showing the third preferred embodiment of the method for fabricating a nonvolatile ferroelectric memory in accordance with the present invention. The third preferred embodiment of a method for fabricating a nonvolatile ferroelectric memory can be used, for example, to fabricate the nonvolatile ferroelectric memory of FIG. 14.

Figure 15A:
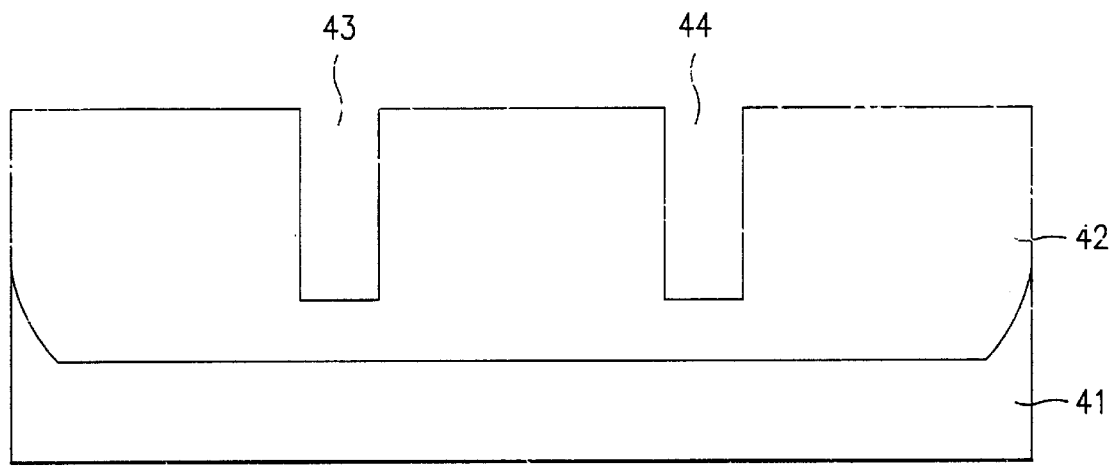
FIGS. 15A~15D are diagrams that illustrate cross-sections showing a method for fabricating a nonvolatile ferroelectric memory in accordance with yet another preferred embodiment of the present invention.
Figure 15B:
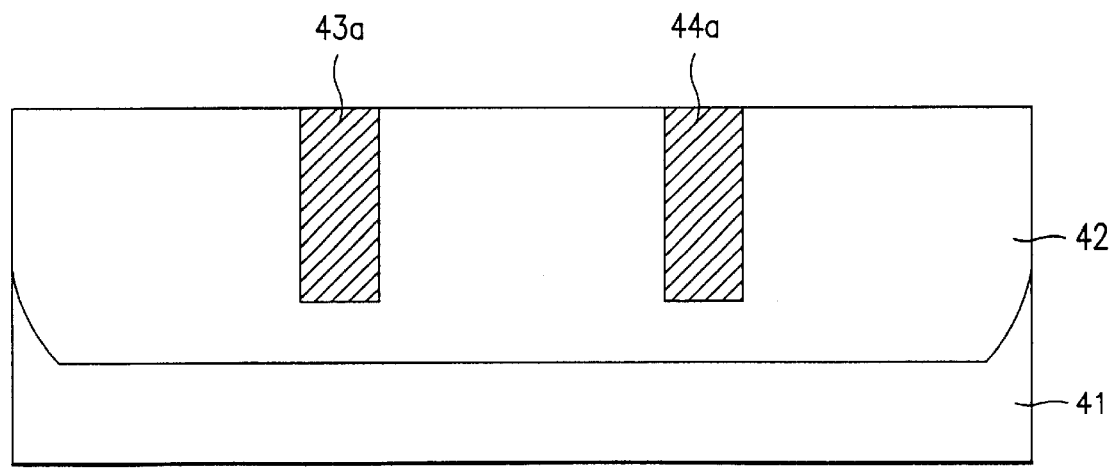

As shown in FIG. 15A, a first conduction type well region 42 is formed down to a prescribed depth from a surface of the first conduction type semiconductor substrate 41. The semiconductor substrate 41 in the well region 42 is etched to form a first and a second trenches 43 and 44. As shown in FIG. 15B, an insulating material is provided to fill in the first and second trenches 43 and 44 and form a first and a second insulating layers 43a and 44a, which separate the well region 42 in a vertical direction.

Figure 15C:
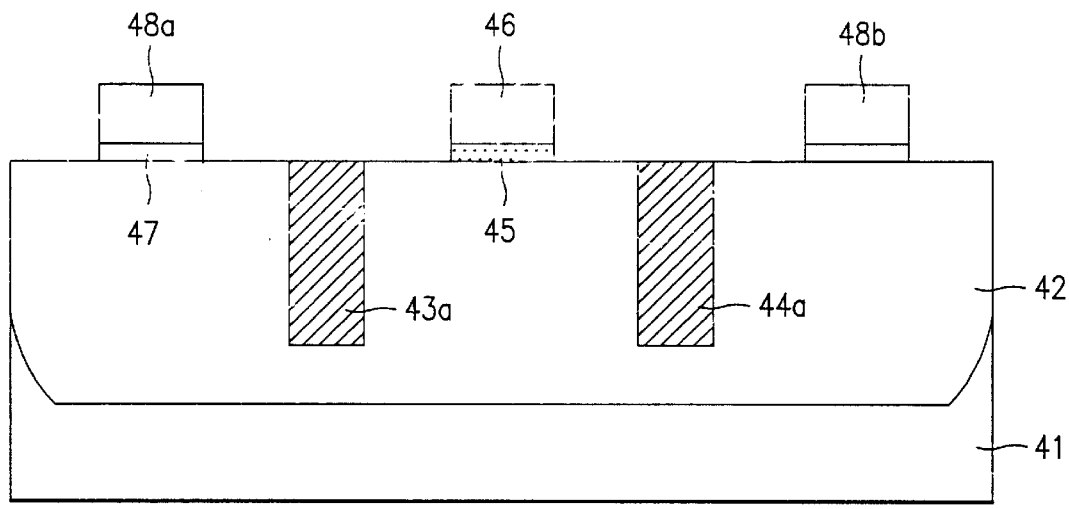

As shown in FIG. 15C, a first gate electrode 46 is formed over the well region 42 between the first insulating layer 43a and the second insulating layer 44a with a ferroelectric material disposed inbetween. Second and third gate electrodes 48a and 48b are formed over other well regions separated by the first and second insulating layers 43a and 44a on both sides of the well region 42 having the first gate electrode 46 formed thereon. Each of the second and third gate electrodes are formed on a gate insulating film 47.

Figure 15D:
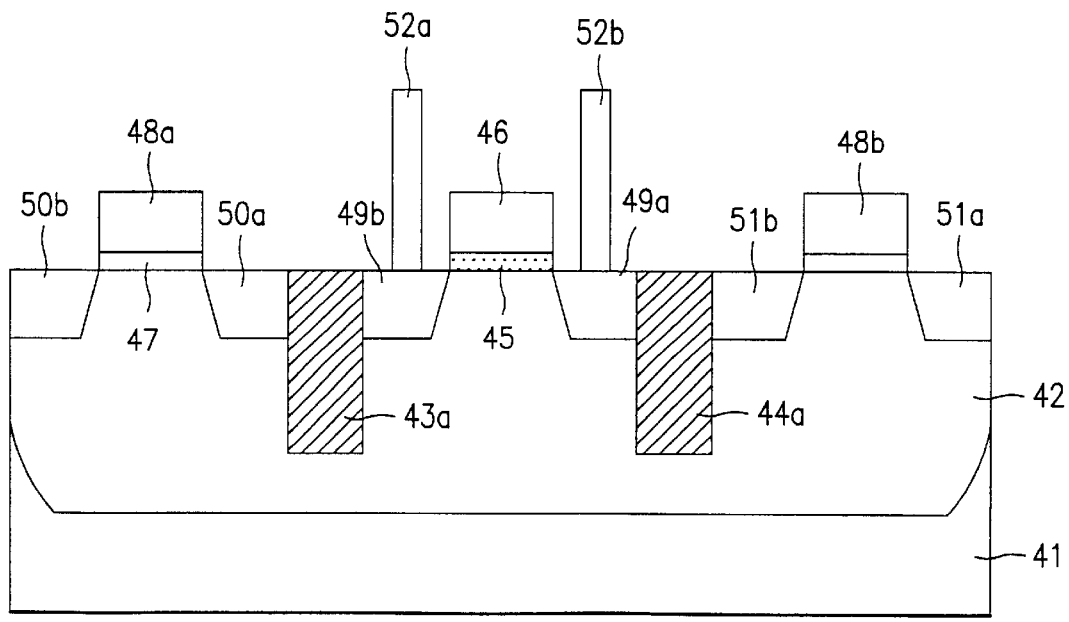

As shown in FIG. 15D, the first, second, and third gate electrodes 46, 48a, and 48b are preferably used as masks in implanting impurity ions to form first source/drain regions 49a/49b in the well region 42 on both sides of the first gate electrode 48b. At the same time, second and third source/drain regions 50a/50b and 51a/51b are preferably formed in the well region 42 on both sides of the second and third gate electrodes 48a and 48b. A first interconnection layer 52a is formed for providing a power source voltage to the first drain region 49b, and a second interconnection layer 52b is formed for electrically coupling the first source region 49a to the second source region 50a. A third interconnection layer (not shown) is preferably formed for electrically coupling the first gate electrode 46 to the third source region 51a.

As described above, preferred embodiments of a nonvolatile ferroelectric memory and a method for fabricating the same have various advantages. A non-destructive memory cell operation can reduce degradation of the ferroelectric material caused by excessive switching. Further, by providing two additional transistors such as NMOS transistors, an operational voltage can be reduced and an operation speed can be increased.

The foregoing embodiments and advantages ate merely exemplary and are not to be construed as limiting the present invention. The present teaching can be readily applied to other types of apparatuses. The description of the present invention is intended to be illustrative, and not to limit the scope of the claims. Many alternatives, modifications, and variations will be apparent to those skilled in the art. In the claims, means-plus-function clauses are intended to cover the structures described herein as performing the recited function and not only structural equivalents but also equivalent structures.

What is claimed is:

1. A method for fabricating a storage device, comprising:
    forming a semiconductor substrate;
    forming a plurality of first signal lines extending along a first direction;
    forming a plurality of second signal lines extending along a second direction to cross the first signal lines; and
    forming a storage cell coupled at a corresponding intersection of the first signal lines and the second signal lines, wherein forming the storage cell comprises,
        forming an insulating layer that divides the substrate into first, second and third regions;
        forming a first gate electrode over a first region of the substrate;
        forming a second gate electrode and a third gate electrode over second and third regions of the substrate on opposite sides of the first gate electrode, respectively, each with a gate insulating film disposed therebetween;
        forming first source/drain regions in the first region of the substrate on both sides of the first gate electrode; and
        forming second and third source/drain regions on both sides of the second and third gate electrodes in the second and third regions of the substrate, respectively.

2. The method of claim 1, comprising:
    forming a first insulating layer at a depth in a semiconductor substrate in a horizontal direction, and forming a second insulating layer arranged from a surface of the substrate to ends of the first insulating layer, to define the first region of the substrate as a first substrate, wherein the second and third regions of the substrate form a second substrate that surrounds a bottom and both sides of the insulating layer; and forming a first impurity region of a conduction type identical to the first substrate in the first substrate on one side of the first source region.

3. The method of claim 2, further comprising forming a second impurity region of a conduction type opposite to the first drain region in the first drain region, wherein the first insulating layer is formed by implanting impurities of a conduction type opposite to the semiconductor substrate, and wherein forming the second insulating layer comprises:

removing the semiconductor substrate to a depth to form two trenches; and filling an insulating material in the trenches.

4. The method of claim 1, further comprising:

forming a first interconnection layer for coupling a power source voltage to the first drain region;

forming a second interconnection layer for electrically coupling the first source region to the second source region; and forming a third interconnection layer for electrically coupling the first gate electrode and the third source region.

5. The method of claim 1, comprising:

forming a well region down to a depth in a semiconductor substrate; and forming first and second insulating layers at fixed intervals to separate the well region in a vertical direction, wherein the first gate electrode is over the well region between the first and second insulation layers, and wherein the second gate electrode and the third gate electrode are over the second and third regions separated by the first and second insulating layers on both sides of the well region having the first gate electrode formed thereon.

6. A method of fabricating a storage device, comprising:

forming a plurality of first signal lines extending along a first direction;

forming a plurality of second signal line pairs extending along a second direction to cross the first signal lines at prescribed intervals;

forming a storage cell coupled at a corresponding intersection of the first signal lines and the pairs of second signal lines, wherein forming the storage cell comprises, forming a first transistor coupled between each pair of the second signal line pairs having a second electrode coupled to a first reference voltage, forming a second transistor having a second electrode coupled to one of the second signal line pairs, a first electrode coupled to a first electrode of the first transistor, and a control electrode coupled to a corresponding first signal line; and forming a third transistor having a second electrode coupled to the other one of the second signal line pairs, a first electrode coupled to a control electrode of the first transistor, and a control electrode coupled to the corresponding first signal line.

7. The method of claim 6, wherein control electrode dielectric films of the first transistors are ferroelectric material, and wherein control electrode dielectric films of the second and third transistors are not a ferroelectric gate insulating material.

8. The method of claim 6, wherein the first transistor is a ferroelectric NMOS transistor having a ferroelectric material gate dielectric film and the second and third transistors are conventional NMOS transistors.

9. The method of claim 6, wherein forming the storage cell comprises an insulating layer that divides a substrate into first, second and third regions under the first, second and third transistors, respectively.

10. The method of claim 9, wherein the insulating layer surrounds sides and a bottom of the first region.

11. The method of claim 10, comprising forming a second semiconductor substrate that surrounds the sides and the bottom of the insulating layer being the second and third regions of the substrate, wherein the first gate electrode is over the first semiconductor substrate, wherein the first source/drain regions of the first transistor are a conduction type opposite to the first semiconductor substrate and respective second and third source/drain regions of the second and third transistor are a conduction type opposite to the second semiconductor substrate.

12. The method of claim 10, wherein a first semiconductor substrate is the first region, comprising forming a first impurity region of a conduction type identical to the first semiconductor substrate in a surface of the first semiconductor substrate on one side of the first source region.

13. The method of claim 10, comprising forming a second impurity region of a conduction type identical to a first semiconductor substrate formed in the first drain region.

14. The method of claim 9, comprising forming a first conduction type well region having a prescribed depth in the substrate; and wherein the insulating layer includes a first and a second insulating layers that separate the well region in a vertical direction at fixed intervals into the first, second and third regions, wherein the first region is between the first and second insulating layers.

15. The method of claim 6, comprising:

forming a first interconnection layer that provides the first reference voltage to the second electrode of the first transistor;

forming a second interconnection layer that electrically couples the first electrode of the first transistor to the first electrode of the second transistor; and forming a third interconnection layer that electrically couples the control electrode of the first transistor and the first electrode of the third transistor.

16. The method of claim 1, wherein the forming a first gate electrode comprises forming the first gate electrode over a ferroelectric gate insulating film disposed over the first region of the substrate.

17. The method of claim 1, comprising:

forming a plurality of first signal lines extending along a first direction;

forming a plurality of second signal line pairs extending along a second direction to cross the first signal lines at prescribed intervals;

forming a storage cell coupled at a corresponding intersection of the first signal lines and the pairs of second signal lines, wherein forming the storage cell comprises, forming a first transistor coupled between each pair of the second signal line pairs having a second electrode coupled to a first reference voltage, forming a second transistor having a second electrode coupled to one of the second signal line pairs, a first electrode coupled to a first electrode of the first transistor, and a control electrode coupled to a corresponding first signal line; and forming a third transistor having a second electrode coupled to the other one of the second signal line pairs, a first electrode coupled to a control electrode of the first transistor, and a control electrode coupled to the corresponding first signal line.

18. The method of claim 17, wherein the first transistor uses the first gate electrode and source/drain regions, wherein the second transistor uses the second gate electrode and source/drain regions, and wherein the third transistor uses the third gate electrode and source/drain regions.

19. The method of claim 1, wherein each of the second signal lines are signal line pairs including a control line and a sensing line.

20. A method for fabricating a storage device, comprising:

forming a semiconductor substrate;

forming an insulating layer that divides the substrate into first, second and third regions;

forming a first gate electrode over a first region of the substrate;

forming a second gate electrode and a third gate electrode over second and third regions of the substrate on opposite sides of the first gate electrode, respectively, each with a gate insulating film disposed therebetween;

forming first source/drain regions in the first region of the substrate on both sides of the first gate electrode; and forming second and third source/drain regions on both sides of the second and third gate electrodes in the second and third regions of the substrate, respectively;

forming a first interconnection layer for coupling a power source voltage to the first drain region;

forming a second interconnection layer for electrically coupling the first source region to the second source region; and forming a third interconnection layer for electrically coupling the first gate electrode and the third source region.

21. The method of claim 20, wherein dielectric films of the first gate electrode are ferroelectric material.

22. The method of claim 20, comprising:

forming a plurality of first signal lines extending along a first direction;

forming a plurality of second signal line pairs extending along a second direction to cross the first signal lines at prescribed intervals;

forming a storage cell coupled at a corresponding intersection of the first signal lines and the pairs of second signal lines, wherein forming the storage cell comprises, forming a first transistor coupled between each pair of the second signal line pairs having a second electrode coupled to a first reference voltage, forming a second transistor having a second electrode coupled to one of the second signal line pairs, a first electrode coupled to a first electrode of the first transistor, and a control electrode coupled to a corresponding first signal line; and forming a third transistor having a second electrode coupled to the other one of the second signal line pairs, a first electrode coupled to a control electrode of the first transistor, and a control electrode coupled to the corresponding first signal line.

* * * * *